(12) United States Patent
Kurtz et al.

(10) Patent No.: US 9,044,303 B2
(45) Date of Patent: Jun. 2, 2015

(54) PRECISE TARGETING OF SURGICAL PHOTODISRUPTION

(71) Applicant: Alcon LenSx, Inc., Aliso Viejo, CA (US)

(72) Inventors: Ronald M. Kurtz, Irvine, CA (US); Ferenc Raksi, Mission Viejo, CA (US); Michael Karavitis, San Pedro, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 0 days.

(21) Appl. No.: 14/138,170

(22) Filed: Dec. 23, 2013

(65) Prior Publication Data

US 2014/0188093 A1    Jul. 3, 2014

Related U.S. Application Data

(63) Continuation of application No. 12/205,844, filed on Sep. 5, 2008, now Pat. No. 8,764,737.

(60) Provisional application No. 60/970,477, filed on Sep. 6, 2007.

(51) Int. Cl.
| | | |
|---|---|---|
| *A61F 9/008* | (2006.01) | |
| *A61B 18/20* | (2006.01) | |
| *A61B 5/00* | (2006.01) | |
| *A61B 17/00* | (2006.01) | |
| *A61B 19/00* | (2006.01) | |
| *A61F 9/009* | (2006.01) | |

(52) U.S. Cl.
CPC ............ *A61F 9/00825* (2013.01); *A61B 5/0066* (2013.01); *A61B 18/20* (2013.01); *A61B 2017/00057* (2013.01); *A61B 2019/5276* (2013.01); *A61B 2019/5437* (2013.01); *A61B 2560/0233* (2013.01); *A61F 9/009* (2013.01); *A61F 2009/00844* (2013.01); *A61F 2009/0087* (2013.01); *A61F 2009/00872* (2013.01); *A61F 2009/00897* (2013.01)

(58) Field of Classification Search
None
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A | 8/1985 | Ishikawa |
| 4,538,608 A | 9/1985 | L'Esperance, Jr. |
| 4,554,917 A | 11/1985 | Tagnon |
| 4,635,299 A | 1/1987 | MacGovern |
| 4,638,801 A | 1/1987 | Daly et al. |
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,112,328 A | 5/1992 | Taboada et al. |
| 5,139,022 A | 8/1992 | Lempert |
| 5,246,435 A | 9/1993 | Bille et al. |
| 5,255,025 A | 10/1993 | Volk |
| 5,286,964 A | 2/1994 | Fountain |
| 5,321,501 A | 6/1994 | Swanson et al. |
| 5,336,215 A | 8/1994 | Hsueh et al. |
| 5,391,165 A | 2/1995 | Fountain et al. |
| 5,439,462 A | 8/1995 | Bille et al. |
| 5,493,109 A | 2/1996 | Wei et al. |
| 5,541,951 A | 7/1996 | Juhasz et al. |
| 5,548,234 A | 8/1996 | Turi et al. |
| 5,549,632 A | 8/1996 | Lai |
| 5,561,678 A | 10/1996 | Juhasz et al. |
| 5,656,186 A | 8/1997 | Mourou et al. |
| 5,738,676 A | 4/1998 | Hammer et al. |
| 5,779,696 A | 7/1998 | Berry et al. |
| 5,789,734 A | 8/1998 | Torigoe et al. |
| 5,795,295 A | 8/1998 | Hellmuth et al. |
| 5,936,706 A | 8/1999 | Takagi |
| 5,954,648 A | 9/1999 | Van Der Brug |
| 5,954,711 A | 9/1999 | Ozaki et al. |
| 5,994,690 A | 11/1999 | Kulkarni et al. |
| 6,004,314 A | 12/1999 | Wei et al. |
| 6,081,543 A | 6/2000 | Liu et al. |
| 6,095,648 A | 8/2000 | Birngruber et al. |
| 6,099,522 A | 8/2000 | Knopp et al. |
| 6,137,585 A | 10/2000 | Hitzenberger et al. |
| 6,203,539 B1 | 3/2001 | Shimmick et al. |
| 6,220,707 B1 | 4/2001 | Bille |

(Continued)

FOREIGN PATENT DOCUMENTS

| | | |
|---|---|---|
| DE | 10307741 | 9/2004 |
| DE | 10 2005 013949 | 9/2006 |

(Continued)

OTHER PUBLICATIONS

Aslyo-Vogel et al., "Darstellung von LTK-Läsionen durch optische Kurzkohärenztomographie (OCT) und Polarisationsmikroskopie nach Sirius-Rot-Fäbung", Ophthalmologe, pp. 487-491, 7-97, (1997).

(Continued)

*Primary Examiner* — H. Sarah Park

(57) ABSTRACT

Techniques, apparatus and systems for laser surgery including imaging-guided surgery techniques, apparatus and systems.

13 Claims, 20 Drawing Sheets

(56) References Cited

U.S. PATENT DOCUMENTS

| | | |
|---|---|---|
| 6,254,595 B1 | 7/2001 | Juhasz et al. |
| 6,288,784 B1 | 9/2001 | Hitzenberger et al. |
| 6,314,311 B1 | 11/2001 | Williams et al. |
| 6,317,616 B1 | 11/2001 | Glossop |
| 6,324,191 B1 | 11/2001 | Horvath |
| 6,337,925 B1 | 1/2002 | Cohen et al. |
| 6,377,349 B1 | 4/2002 | Fercher |
| 6,379,005 B1 | 4/2002 | Williams et al. |
| 6,451,009 B1 | 9/2002 | Dasilva et al. |
| 6,454,761 B1 | 9/2002 | Freedman |
| 6,497,701 B2 | 12/2002 | Shimmick et al. |
| 6,529,758 B2 | 3/2003 | Shahidi |
| 6,579,282 B2 | 6/2003 | Bille et al. |
| 6,610,050 B2 | 8/2003 | Bille |
| 6,610,051 B2 | 8/2003 | Bille |
| 6,623,476 B2 | 9/2003 | Juhasz et al. |
| 6,687,010 B1 | 2/2004 | Horii et al. |
| 6,693,927 B1 | 2/2004 | Horvath et al. |
| 6,726,680 B1 | 4/2004 | Knopp et al. |
| 6,730,074 B2 | 5/2004 | Bille et al. |
| 6,741,359 B2 | 5/2004 | Wei et al. |
| 6,746,121 B2 | 6/2004 | Ross et al. |
| 6,751,033 B2 | 6/2004 | Goldstein et al. |
| 6,755,819 B1 | 6/2004 | Waelti |
| 6,763,259 B1 | 7/2004 | Hauger et al. |
| 6,769,769 B2 | 8/2004 | Podoleanu et al. |
| 6,775,007 B2 | 8/2004 | Izatt et al. |
| 6,863,667 B2 | 3/2005 | Webb et al. |
| 6,887,232 B2 | 5/2005 | Bille |
| 6,899,707 B2 | 5/2005 | Scholler et al. |
| 6,908,196 B2 | 6/2005 | Herekar et al. |
| 6,932,807 B1 | 8/2005 | Tomita et al. |
| 6,991,629 B1 | 1/2006 | Juhasz et al. |
| 6,992,765 B2 | 1/2006 | Horvath et al. |
| 6,996,905 B2 | 2/2006 | Meguro |
| 7,006,232 B2 | 2/2006 | Rollins et al. |
| 7,018,376 B2 | 3/2006 | Webb et al. |
| 7,027,233 B2 | 4/2006 | Goldstein et al. |
| 7,061,622 B2 | 6/2006 | Rollins et al. |
| 7,072,047 B2 | 7/2006 | Rollins et al. |
| 7,079,254 B2 | 7/2006 | Kane et al. |
| 7,102,756 B2 | 9/2006 | Izatt et al. |
| 7,113,818 B2 | 9/2006 | Podoleanu et al. |
| 7,126,693 B2 | 10/2006 | Everett et al. |
| 7,130,054 B2 | 10/2006 | Ostrovsky et al. |
| 7,131,968 B2 | 11/2006 | Bendett et al. |
| 7,133,137 B2 | 11/2006 | Shimmick |
| 7,139,077 B2 | 11/2006 | Podoleanu et al. |
| 7,145,661 B2 | 12/2006 | Hitzenberger |
| 7,148,970 B2 | 12/2006 | de Boer |
| 7,184,148 B2 | 2/2007 | Alphonse |
| 7,207,983 B2 | 4/2007 | Hahn et al. |
| 7,248,371 B2 | 7/2007 | Chan et al. |
| 7,268,885 B2 | 9/2007 | Chan et al. |
| 7,280,221 B2 | 10/2007 | Wei |
| 7,307,733 B2 | 12/2007 | Chan et al. |
| 7,310,150 B2 | 12/2007 | Guillermo et al. |
| 7,312,876 B2 | 12/2007 | Chan et al. |
| 7,319,566 B2 | 1/2008 | Prince et al. |
| 7,329,002 B2 | 2/2008 | Nakanishi |
| 7,330,270 B2 | 2/2008 | O'Hara et al. |
| 7,330,273 B2 | 2/2008 | Podoleanu et al. |
| 7,330,275 B2 | 2/2008 | Raksi |
| 7,335,223 B2 | 2/2008 | Obrebski |
| 7,336,366 B2 | 2/2008 | Choma et al. |
| 7,342,659 B2 | 3/2008 | Horn et al. |
| 7,347,548 B2 | 3/2008 | Huang et al. |
| 7,352,444 B1 | 4/2008 | Seams et al. |
| 7,355,716 B2 | 4/2008 | de Boer et al. |
| 7,364,296 B2 | 4/2008 | Miller et al. |
| 7,365,856 B2 | 4/2008 | Everett et al. |
| 7,365,859 B2 | 4/2008 | Yun et al. |
| 7,370,966 B2 | 5/2008 | Fukuma et al. |
| 7,371,230 B2 | 5/2008 | Webb et al. |
| 7,372,578 B2 | 5/2008 | Akiba et al. |
| 7,388,672 B2 | 6/2008 | Zhou et al. |
| 7,390,089 B2 | 6/2008 | Loesel et al. |
| 7,400,410 B2 | 7/2008 | Baker et al. |
| 7,402,159 B2 | 7/2008 | Loesel et al. |
| 7,426,037 B2 | 9/2008 | Ostrovsky et al. |
| 7,433,046 B2 | 10/2008 | Everett et al. |
| 7,452,077 B2 | 11/2008 | Meyer et al. |
| 7,452,080 B2 | 11/2008 | Wiltberger et al. |
| 7,452,081 B2 | 11/2008 | Wiltberger et al. |
| 7,461,658 B2 | 12/2008 | Jones et al. |
| 7,466,423 B2 | 12/2008 | Podoleanu et al. |
| 7,470,025 B2 | 12/2008 | Iwanaga |
| 7,477,764 B2 | 1/2009 | Haisch |
| 7,480,058 B2 | 1/2009 | Zhao et al. |
| 7,480,059 B2 | 1/2009 | Zhou et al. |
| 7,488,070 B2 | 2/2009 | Hauger et al. |
| 7,488,930 B2 | 2/2009 | Ajgaonkar et al. |
| 7,492,466 B2 | 2/2009 | Chan et al. |
| 7,503,916 B2 | 3/2009 | Shimmick |
| 7,508,525 B2 | 3/2009 | Zhou et al. |
| 7,522,642 B2 | 4/2009 | Zadoyan et al. |
| 7,535,577 B2 | 5/2009 | Podoleanu et al. |
| 7,537,591 B2 | 5/2009 | Feige et al. |
| 7,557,928 B2 | 7/2009 | Ueno |
| 7,575,322 B2 | 8/2009 | Somani |
| 7,584,756 B2 | 9/2009 | Zadoyan et al. |
| 7,593,559 B2 | 9/2009 | Toth et al. |
| 7,597,444 B2 | 10/2009 | Rathjen et al. |
| 7,599,591 B2 | 10/2009 | Andersen et al. |
| 7,602,500 B2 | 10/2009 | Izatt et al. |
| 7,604,351 B2 | 10/2009 | Fukuma et al. |
| 7,614,744 B2 | 11/2009 | Abe |
| 7,630,083 B2 | 12/2009 | de Boer et al. |
| 7,631,970 B2 | 12/2009 | Wei |
| 7,633,627 B2 | 12/2009 | Choma et al. |
| 7,643,152 B2 | 1/2010 | de Boer et al. |
| 7,655,002 B2 | 2/2010 | Myers |
| 7,797,119 B2 | 9/2010 | De Boer et al. |
| 7,813,644 B2 | 10/2010 | Chen et al. |
| 7,898,712 B2 | 3/2011 | Adams et al. |
| 7,918,559 B2 | 4/2011 | Tesar |
| 8,246,609 B2 | 8/2012 | Zickler et al. |
| 8,262,646 B2 | 9/2012 | Frey et al. |
| 8,394,084 B2 | 3/2013 | Palankar et al. |
| 2001/0022648 A1 | 9/2001 | Lai |
| 2002/0013574 A1 | 1/2002 | Elbrecht et al. |
| 2002/0082466 A1 | 6/2002 | Han |
| 2002/0097374 A1 | 7/2002 | Payne et al. |
| 2002/0133145 A1 | 9/2002 | Gerlach et al. |
| 2002/0198516 A1 | 12/2002 | Knopp |
| 2003/0053219 A1 | 3/2003 | Manzi |
| 2003/0090674 A1 | 5/2003 | Zeylikovich et al. |
| 2003/0206272 A1 | 11/2003 | Cornsweet et al. |
| 2004/0039378 A1 | 2/2004 | Lin |
| 2004/0059321 A1 | 3/2004 | Knopp et al. |
| 2004/0151466 A1 | 8/2004 | Crossman-Bosworth et al. |
| 2004/0202351 A1 | 10/2004 | Park et al. |
| 2004/0243112 A1 | 12/2004 | Bendett et al. |
| 2004/0243233 A1 | 12/2004 | Phillips |
| 2004/0254568 A1 | 12/2004 | Rathjen |
| 2005/0010109 A1 | 1/2005 | Faul |
| 2005/0015120 A1 | 1/2005 | Seibel et al. |
| 2005/0021011 A1 | 1/2005 | LaHaye |
| 2005/0173817 A1 | 8/2005 | Fauver et al. |
| 2005/0192562 A1 | 9/2005 | Loesel et al. |
| 2005/0201633 A1 | 9/2005 | Moon et al. |
| 2005/0203492 A1 | 9/2005 | Nguyen et al. |
| 2005/0215986 A1 | 9/2005 | Chernyak et al. |
| 2005/0228366 A1 | 10/2005 | Kessler et al. |
| 2005/0274894 A1 | 12/2005 | Fujita |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0077346 A1 | 4/2006 | Matsumoto |
| 2006/0084954 A1 | 4/2006 | Zadoyan et al. |
| 2006/0100613 A1 | 5/2006 | McArdle et al. |
| 2006/0179992 A1 | 8/2006 | Kermani |
| 2006/0187462 A1 | 8/2006 | Srinivasan |

(56) References Cited

U.S. PATENT DOCUMENTS

| | | |
|---|---|---|
| 2006/0195076 A1 | 8/2006 | Blumenkranz et al. |
| 2006/0206102 A1 | 9/2006 | Shimmick |
| 2007/0013867 A1 | 1/2007 | Ichikawa |
| 2007/0106285 A1 | 5/2007 | Raksi |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173791 A1 | 7/2007 | Raksi |
| 2007/0173794 A1 | 7/2007 | Frey et al. |
| 2007/0173795 A1 | 7/2007 | Frey et al. |
| 2007/0173796 A1 | 7/2007 | Kessler et al. |
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0235543 A1 | 10/2007 | Zadoyan et al. |
| 2007/0282313 A1 | 12/2007 | Huang et al. |
| 2007/0291277 A1 | 12/2007 | Everett et al. |
| 2007/0299429 A1 | 12/2007 | Amano |
| 2008/0015553 A1 | 1/2008 | Zacharias |
| 2008/0033406 A1 | 2/2008 | Andersen et al. |
| 2008/0049188 A1 | 2/2008 | Wiltberger et al. |
| 2008/0055543 A1 | 3/2008 | Meyer et al. |
| 2008/0056610 A1 | 3/2008 | Kanda |
| 2008/0071254 A1 | 3/2008 | Lummis et al. |
| 2008/0077121 A1 | 3/2008 | Rathjen |
| 2008/0088795 A1 | 4/2008 | Goldstein et al. |
| 2008/0100612 A1 | 5/2008 | Dastmalchi et al. |
| 2008/0147052 A1 | 6/2008 | Bendett et al. |
| 2008/0167642 A1 | 7/2008 | Palanker et al. |
| 2008/0192783 A1 | 8/2008 | Rathjen et al. |
| 2008/0228176 A1 | 9/2008 | Triebel et al. |
| 2008/0231807 A1 | 9/2008 | Lacombe et al. |
| 2008/0269731 A1 | 10/2008 | Swinger et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2008/0319428 A1 | 12/2008 | Wiechmann et al. |
| 2008/0319464 A1 | 12/2008 | Bischoff et al. |
| 2009/0002835 A1 | 1/2009 | Prior et al. |
| 2009/0012507 A1 | 1/2009 | Culbertson et al. |
| 2009/0088734 A1 | 4/2009 | Mordaunt |
| 2009/0118718 A1 | 5/2009 | Raksi et al. |
| 2009/0125005 A1 | 5/2009 | Chernyak et al. |
| 2009/0131921 A1 | 5/2009 | Kurtz et al. |
| 2009/0149742 A1 | 6/2009 | Kato et al. |
| 2009/0149841 A1 | 6/2009 | Kurtz |
| 2009/0157062 A1 | 6/2009 | Hauger |
| 2009/0161827 A1 | 6/2009 | Gertner et al. |
| 2009/0168017 A1 | 7/2009 | O Hara et al. |
| 2009/0171327 A1 | 7/2009 | Kurtz et al. |
| 2009/0177189 A1 | 7/2009 | Raksi |
| 2009/0231704 A1 | 9/2009 | Chen |
| 2009/0268161 A1 | 10/2009 | Hart et al. |
| 2009/0296083 A1 | 12/2009 | Saaski et al. |
| 2009/0299347 A1 | 12/2009 | Vogler et al. |
| 2010/0004641 A1 | 1/2010 | Frey et al. |
| 2010/0004643 A1 | 1/2010 | Frey et al. |
| 2010/0007848 A1 | 1/2010 | Murata |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0082017 A1 | 4/2010 | Zickler et al. |
| 2010/0110377 A1 | 5/2010 | Maloca et al. |
| 2010/0130966 A1 | 5/2010 | Brownell |
| 2010/0191226 A1 | 7/2010 | Blumenkranz et al. |
| 2010/0324543 A1 | 12/2010 | Kurtz et al. |
| 2011/0022036 A1 | 1/2011 | Frey et al. |
| 2011/0034911 A1 | 2/2011 | Bischoff et al. |
| 2011/0118609 A1 | 5/2011 | Goldshleger et al. |
| 2011/0184392 A1 | 7/2011 | Culbertson et al. |
| 2011/0196350 A1 | 8/2011 | Friedman et al. |
| 2011/0202044 A1 | 8/2011 | Goldshleger et al. |
| 2011/0222020 A1 | 9/2011 | Izatt et al. |
| 2011/0264081 A1 | 10/2011 | Reich et al. |
| 2011/0319873 A1 | 12/2011 | Raksi et al. |

FOREIGN PATENT DOCUMENTS

| | | |
|---|---|---|
| EP | 0326760 | 8/1989 |
| EP | 0697611 | 2/1996 |
| EP | 1279386 | 1/2003 |
| EP | 1444946 | 8/2004 |
| EP | 1584310 | 10/2005 |
| EP | 1837696 | 9/2007 |
| EP | 2322083 | 5/2011 |
| JP | 4-503913 | 7/1992 |
| JP | 2002345758 | 12/2001 |
| JP | 2004-531344 | 10/2004 |
| JP | 2007-159740 | 6/2007 |
| JP | 2009-523556 | 6/2009 |
| WO | 90/09141 | 8/1990 |
| WO | 98/08048 | 2/1998 |
| WO | WO9808048 | 2/1998 |
| WO | 98/56298 | 12/1998 |
| WO | 03/002008 | 1/2003 |
| WO | 03/062802 | 7/2003 |
| WO | 2004/049228 | 6/2004 |
| WO | 2006074469 | 7/2006 |
| WO | 2007/021022 | 2/2007 |
| WO | 2007/056486 | 5/2007 |
| WO | 2007/084694 | 7/2007 |
| WO | WO2007106326 | 9/2007 |
| WO | 2007130411 | 11/2007 |
| WO | 2008/055506 | 5/2008 |
| WO | 2009/089504 | 7/2009 |
| WO | 2010/075571 | 7/2010 |

OTHER PUBLICATIONS

Bagayev et al., "Optical coherence tomography for in situ monitoring of laser corneal ablation", Journal of Biomedical Optics, 7(4), pp. 633-642 (Oct. 2002).

Blaha et al., "The slit lamp and the laser in ophthalmology—a new laser slit lamp", SPIE Optical Instrumentation for Biomedical Laser Applications, vol. 658, pp. 38-42, 1986.

Boppart, S., et al., "Intraoperative Assessment of Microsurgery with Three-dimensional Optical Coherence Tomography", Radiology, 208(1):81-86, Jul. 1998.

Davidson, "Analytic Waveguide Solutions and the Coherence Probe Microscope", Microelectronic Engineering, 13, pp. 523-526, 1991.

Drexler, W., et al., "Measurement of the thickness of fundus layers by partial coherence tomography", Optical Engineering, 34(3):701-710, Mar. 1995.

Dyer, P., et al., "Optical Fibre Delivery and Tissue Ablation Studies using a Pulsed Hydrogen Fluoride Laser", Lasers in Medical Science, 7:331-340, 1992.

Fercher et al., "In Vivo Optical Coherence Tomography", American Journal of Ophthalmology, 116(1), pp. 113-114, 1993.

Fujimoto, J., et al., :Biomedical Imaging using Optical Coherent Tomography, 1994, 67.

Hammer, D., "Ultrashort pulse laser induced bubble creation thresholds in ocular media", SPIE, 2391:30-40, 1995.

Hauger, C., et al., "High speed low coherence interferometer for optical coherence tomography", Proceedings of SPIE, 4619:1-9, 2002.

Hee, M., et al., "Optical Coherence tomography of the Human Retina", Arch Ophthalmol, 113:325-332; Mar. 1995.

Hitzenberger et al., "Interferometric Measurement of Corneal Thickness With Micrometer Precision", American Journal of Ophthalmology, 118:468-476, Oct. 1994.

Hitzenberger, C., et al., "Retinal layers located with a precision of 5 μm by partial coherence interferometry", SPIE, 2393:176-181, 1995.

Itoh et al., "Absolute measurements of 3-D shape using white-light interferometer", SPIE Interferometry: Techniques and Analysis, 1755:24-28, 1992.

(56) References Cited

OTHER PUBLICATIONS

Izatt et al., "Ophthalmic Diagnostics using Optical Coherence Tomography", SPIE Ophthalmic Technologies, 1877:136-144, 1993.
Izatt, J., et al., "Micrometer-Scale Resolution Imaging of the Anterior Eye In vivo With Optical Coherence Tomography", Arch Ophthalmol, 112:1584-1589, Dec. 1994.
Jean, B., et al., "Topography assisted photoablation", SPIE, vol. 3591:202-208, 1999.
Kamensky, V., et al., "In Situ Monitoring of Laser Modification Process in Human Cataractous Lens and Porcine Cornea Using Coherence Tomography", Journal of biomedical Optics, 4(1), 137-143, Jan. 1999.
Lee et al., "Profilometry with a coherence scanning microscope", Applied Optics, 29(26), 3784-3788, Sep. 10, 1990.
Lubatschowski, "The German Ministry of Research and education funded this OCT guided fs laser surgery in Sep. 2005", http://www.laser-zentrum-hannover.de/download/pdf/taetigkeitsbericht2005.pdf.
Massow, O., et al., "Femtosecond laser microsurgery system controlled by OCT", Laser Zentrum Hannover e.V., The German Ministry of education and research,19 slides, 2007.
Puliafito, Carmen, "Final technical Report: Air Force Grant #F49620-93-I-03337(1)" dated Feb. 12, 1997, 9 pages.
Ren, Q., et al., "Axicon: A New Laser Beam Delivery System for Corneal Surgery", IEEE Journal of Quantum Electronics, 26(12):2305-2308, Dec. 1990.
Ren, Q., et al., "Cataract Surgery with a Mid-Infrared Endo-laser System", SPIE Ophthalmic Technologies II, 1644:188-192, 1992.
Thompson, K., et al., "Therapeutic and Diagnostic Application of Lasers in Ophthalmology", Proceedings of the IEEE, 80(6):838-860, Jun. 1992.
Thrane, L, et al., "Calculation of the maximum obtainable probing depth of optical coherence tomography in tissue", Proceedings of SPIE, 3915:2-11, 2000.
Wisweh, H., et al., "OCT controlled vocal fold femtosecond laser microsurgery", Laser Zentrum Hannover e.V., The German Ministry of education and research, Grants: 13N8710 and 13N8712; 23 slides, 2008.
An, Lin and Wang, Ruikang K., "Use of a scanner to modulate spatial interferograms for in vivo full-range Fourier-domain optical coherence tomography", Dec. 1, 2007, Optics Letters, vol. 32(23); pp. 3423-3425.
European Supplementary European Search Report for EP Application No. 10806836.2 with mailing date Oct. 8, 2012, 4 pages.
Plamann K et al., "Laser parameters, focusing optics, and side effects femtosecond laser corneal surgery" (2008) SPIE vol. 6844.
Duma et al., "Determination of Significant Parameters for Eye Injury Risk from Projectiles", Oct. 2005; Journal of Trauma Injury, Infection, and Critical Care, 59(4):960-4, 5 pages.
Gwon et al., "Focal laser photophacoablation of normal and cataractous lenses in rabbits: Preliminary report," May 1995, J. Cataract Refract Surg, 21:282-286, 5 pages.
Jenkins, Francis A., White, Harvey E., Fundamentals of Optics, 4th Ed., 2001, p. 190-191.
Kruger et al., "Experimental Increase in Accommodative Potential after Neodymium: Yttrium—Aluminum-Garnet Laser," Jun. 2001, Ophthalmology 108:2122-2129, 8 pages.
Lindstrom, Cionni, Donnenfeld, and Slade, "The Dawn of Laser Refractive Cataract Surgery" excerpts from Supplement to Cataract & Refractive Surgery Today, Jun. 2011, 6 pages, Sponsored by Alcon Laboratories, Inc., published in the U.S.
PCT International Application No. PCT/US2010/042777, in International Search Report mailed Mar. 25, 2011, 10 pages.
PCT International Application No. PCT/US2010/042786, in International Search Report mailed Apr. 25, 2011, 9 pages.
PCT International Application No. PCT/US2010/042787, in International Search Report mailed Mar. 25, 2011, 11 pages.
PCT International Application No. PCT/US2010/042791, in International Search Report mailed Mar. 25, 2011, 14 pages.
PCT International Application No. PCT/US2010/042796, in International Search Report mailed Mar. 28, 2011, 11 pages.
PCT International Application No. PCT/US2010/042800, in International Search Report mailed Mar. 30, 2011, 9 pages.
PCT International Application No. PCT/US2010/042804, in International Search Report mailed Mar. 30, 2011, 8 pages.
PCT International Application No. PCT/US2010/042957, in International Search Report mailed Apr. 25, 2011, 9 pages.
PCT International Application No. PCT/US2010/042960, in International Search Report mailed Apr. 25, 2011, 9 pages.
PCT International Application No. PCT/US2010/042964, in International Search Report mailed Apr. 25, 2011, 9 pages.
PCT International Application No. PCT/US2010/055968, in International Search Report mailed Jul. 6, 2011, 9 pages.
Ryan et al., "Nd:YAG Laser Photodisruption of the Lens Nucleus Before Phacoemulsification," Oct. 1987, American Journal of Ophthalmology 104:382-386, 5 pages.
Wang, Haifeng and Gan, Fuxi, 2001, "High focal depth with a pure-phase apodizer", Applied Optics, vol. 40, No. 31, 5658-5662, 5 pages.
PCT International Search Report and Written Opinion dated Apr. 10, 2012 for International Application No. PCT/US/2011/051466, filed Sep. 13, 2011.
PCT International Search Report and Written Opinion dated Feb. 9, 2012 for International Application Serial No. PCT/US2011/040223.
Hee et al.; "Femtosecond transillumination optical coherence tomography"; Optics Letters; vol. 18; No. 12; pp. 950-952 (Jun. 1993).
Kamensky et al.; "In situ monitoring of the middle IR laser ablation of a cataract-suffered human lens by optical coherent tomography"; Proc. SPIE; 2930: 222-229 (1996).
Kamensky et al.; "Monitoring and animation of laser ablation process in cataracted eye lens using coherence IDS 41 tomography"; Proc. SPIE; 2981: 94-102 (1997).
Ostaszewski et al.; "Risley prism beam pointer"; Proc. of SPIE; vol. 6304; 630406-1 through 630406-10, (2006).
PCT International Search Report for International Application Serial No. PCT/US2010/056701 mailed Aug. 24, 2011.
Swanson et al.; "In vivo retinal imaging by optical coherence tomography"; Optics Letters; vol. 18; No. 21; pp. 1864-1866 (Nov. 1993).
European Search Report; European Patent Application Serial No. 10191057.8 mailed Mar. 16, 2011.
Kim, Tae Hoon, Authorized Officer, Korean Intellectual Property Office, PCT International Application No. PCT/US2011/025332, in International Search Report, mailed Sep. 16, 2011, 8 pages.
Kim, Tae Hoon, Authorized Officer, Korean Intellectual Property Office, PCT International Application No. PCT/US2011/023710, in International Search Report, mailed Aug. 24, 2011, 8 pages.
European Patent Office, European Patent Application No. 10191057.8, in European Search Report, mailed Mar. 16, 2011, to be published by the USPTO, 3 pages.
U.S. Appl. No. 90/006,816, filed Feb. 27, 2007, Swanson et al.
Arimoto et al., "Imaging Properties of Axicon in a Scanning Optical System," Nov. 1, 1992, Applied Optics, 31(31): 6652-6657, 5 pages.
Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27, 7 pages.
Stern et al., "Femtosecond Optical Ranging of Corneal Incision Depth," Jan. 1989, Investigative Ophthalmology & Visual Science, 30(1):99-104, 6 pages.
Fercher et al., "Eye-Length Measurement by Interferometry With Partially Coherent Light," Mar. 1988, Optics Letters, 13(3):186-188, 3 pages.
Fercher et al., "Measurement of Intraocular Distances by Backscattering Spectral Interferometry," May 15, 1995, Optics Comm. 117:43-48, 6 pages.
Wojtkowski et al., "In Vivo Human Retinal Imaging by Fourier Domain Optical Coherence Tomography," Jul. 2002, Journal of Biomedical Optics 7(3):457-463, 7 pages.

(56) References Cited

OTHER PUBLICATIONS

Izatt et al., Micron-Resolution Biomedical Imaging With Optical Coherence Tomography, Oct. 1993, Optics & Photonics News, pp. 14-19, 6 pages.

Chinn, S.R., et al., "Optical coherence tomography using a frequency-tunable optical source," *Optics Letters*, 22(5):340-342, Mar. 1997.

Huber, R., et al., "Three-dimensional and C-mode OCT imaging with a compact, frequency swept laser source at 1300 nm," *Optics Express*, 13(26):10523-10538, Dec. 2005.

Yun, S.H., et al., "Wavelength-swept fiber laser with frequency shifted feedback and resonantly swept intra-cavity acoustooptic tunable filter," *IEEE Journal of Selected Topics in Quantum Electronics*, 3(4):1087-1096, Aug. 1997.

Massow, O., et al., "Femtosecond laser microsurgery system controlled by optical coherence tomography," *Proceedings of the SPIE—Commercial and Biomedical Applications of Ultrafast Lasers VIII*, vol. 6881, pp. 688106(1)-688106(6), Mar. 2008.

Massow, O., et al., "Optical coherence tomography controlled femtosecond laser microsurgery system," *Proceedings of the SPIE—Optical Coherence Tomography and Coherence Techniques III*, vol. 6627, pp. 662717(1)-662717(6), Aug. 2007.

Ohmi, M., et al., "In-situ Observation of Tissue Laser Ablation Using Optical Coherence Tomography," *Optical and Quantum Electronics*, 37(13-15):1175-1183, Dec. 2005.

Sarunic, M., et al., "Imaging the Ocular Anterior Segment With Real-Time, Full-Range Fourier-Domain Optical Coherence Tomography," *Archives of Ophthalmology*, 126(4):537-542, Apr. 2008.

Sarunic, M., et al., "Instantaneous complex conjugate resolved spectral domain and swept-source OCT using 3×3 fiber couplers," *Optics Express*, 13(3):957-967, Feb. 2005.

Sarunic, M., et al., "Real-time quadrature projection complex conjugate resolved Fourier domain optical coherence tomography," *Optics Letters*, 31(16):2426-2428, Aug. 2006.

Swanson, et al., "Method and Apparatus for Optical Imaging with Means for Controlling the Longitudinal Range of the Sample," Reexam U.S. Appl. No. 90/006,816, filed Oct. 20, 2003.

Tao, Y., et al., "High-speed complex conjugate resolved retinal spectral domain optical coherence tomography using sinusoidal phase modulation," *Optics Letters*, 32(20):2918-2920, Oct. 2007.

International Search Report and Written Opinion dated Mar. 12, 2009 for International Application No. PCT/US2008/075511, filed Sep. 5, 2008 (9 pages).

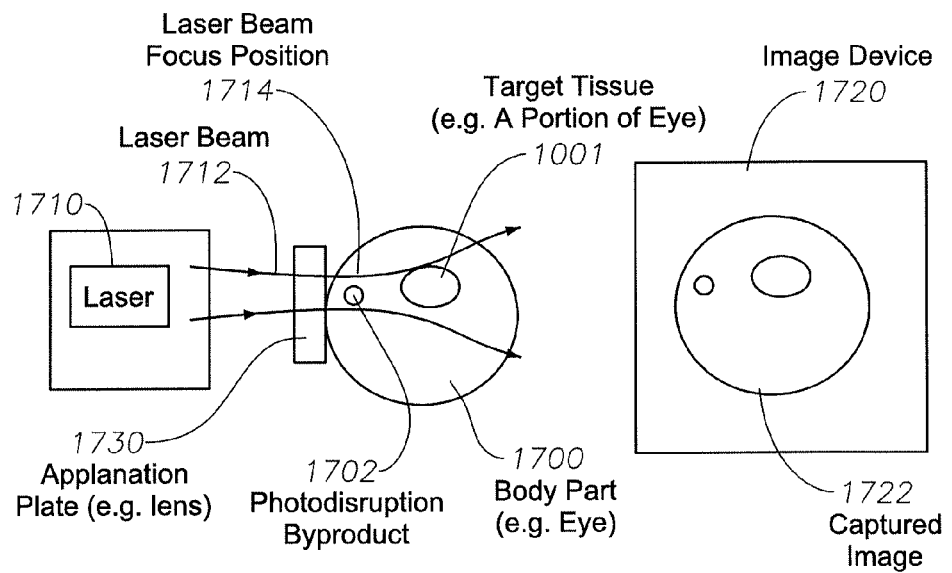
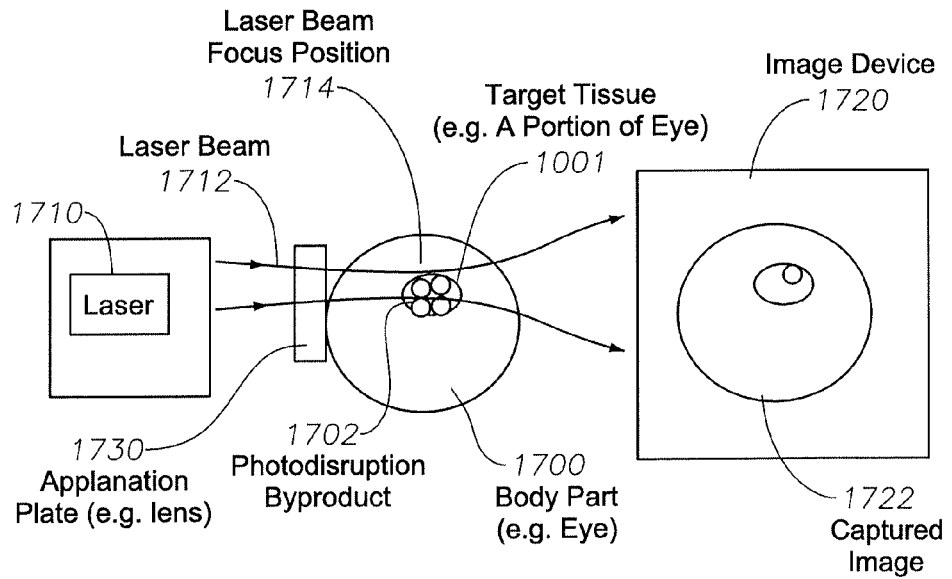

PRECISE TARGETING OF SURGICAL PHOTODISRUPTION

PRIORITY CLAIM AND RELATED PATENT APPLICATION

This patent document is a continuation of co-pending U.S. patent application Ser. No. 12/205,844, filed on Sep. 5, 2008, entitled "Precise Targeting of Surgical Photodisruption" by R. M. Kurtz, F. Raksi and M. Karavitis, that claims priority from and benefit of U.S. Patent Application No. 60/970,477, filed on Sep. 6, 2007, entitled "Precise Targeting of Surgical Photodisruption" by R. M. Kurtz, F. Raksi and M. Karavitis, both patent applications incorporated herein in their entirety by reference as part of the specification of the present patent document.

BACKGROUND

This document relates to laser surgery techniques, apparatus and systems, including laser surgery techniques, apparatus and systems based on photodisruption caused by laser pulses in a tissue.

Laser light can be used to perform various surgical operations in eyes and other tissues in humans and animals. Recent development of laser surgical methods for performing operations on the human eye, such as LASIK combined with flap creation using a femtosecond laser, demonstrates that surgery of the human eye with lasers often requires precision and speed which cannot be achieved by manual and mechanical surgical methods. In laser surgery such as laser ophthalmic surgery, laser pulses interact with a target tissue to cause one or more desired surgical effects in the tissue. One example of surgical effects is the laser-induced photodisruption, a nonlinear optical interaction between light and a tissue that causes the tissue to ionize. Laser-induced photodisruption can be used to selectively remove or disrupt tissue in various surgical procedures, such as laser surgery in ophthalmology. Traditional ophthalmic photodisruptors have used relatively long pulse duration lasers in single shot or burst modes involving a series of approximately a few laser pulses (e.g., three) from a pulsed laser such as a pulsed Nd:YAG laser. Newer laser surgical systems including laser ophthalmic systems tend to operate with short laser pulses with high repetition rates, e.g., thousands of shots per second and relatively low energy per pulse.

One technical challenge associated with surgical lasers of short laser pulses with high repetition rates is precise control and aiming of the laser pulses, e.g., the beam position and beam focusing of the pulses in a surgical laser beam.

SUMMARY

This document describes implementations of techniques, apparatus and systems for laser surgery.

In one aspect, a laser surgical system includes a pulse laser to produce a laser beam of laser pulses; an optics module to receive the laser beam and to focus and direct the laser beam onto a target tissue to cause photodisruption in the target tissue; an applanation plate operable to be in contact with the target tissue to produce an interface and to transmit laser pulses to the target and reflected or scattered light or sound from the target through the interface; an imaging device to capture light or sound from the target to create an image of the target tissue; and a system control module to process imaging information on the image from the imaging device and to control the optics module to adjust the laser beam focus to the target tissue based on the imaging information.

In another aspect, a method for targeting a pulsed laser beam to a target tissue in laser surgery includes monitoring image of target tissue of a body part and image of a reference on the body part to aim the pulsed laser beam at the target tissue; and monitoring images of photodisruption byproduct and the target tissue to adjust the pulsed laser beam to overlap the location of the photodisruption byproduct with the target tissue.

In another aspect, a method for targeting a pulsed laser beam to a target tissue in laser surgery includes monitoring image of target tissue of a body part and image of a reference on the body part to aim the pulsed laser beam at the target tissue; obtaining images of photodisruption byproduct in a calibration material to generate a three-dimensional reference system inside the target tissue; and controlling the focusing and scanning of the surgical laser beam during the surgery in the target tissue based on the three-dimensional reference system.

In another aspect, a method for targeting a pulsed laser beam to a target tissue in laser surgery includes aiming a pulsed laser beam at a target tissue location within target tissue to deliver a sequence of initial alignment laser pulses to the target tissue location; monitoring images of the target tissue location and photodisruption byproduct caused by the initial alignment laser pulses to obtain a location of the photodisruption byproduct relative to the target tissue location; controlling the pulsed laser beam to carry surgical laser pulses at the surgical pulse energy level; adjusting a position of the pulsed laser beam at the surgical pulse energy level to place the location of photodisruption byproduct at the determined location; and, while monitoring images of the target tissue and the photodisruption byproduct, continuing to adjust position of the pulsed laser beam at the surgical pulse energy level to place the location of photodisruption byproduct at a respective determined location when moving the pulsed laser beam to a new target tissue location within the target tissue.

In another aspect, a laser surgical system includes a pulsed laser to produce a pulsed laser beam; a beam control optical module that directs the pulsed laser beam at a target tissue location within target tissue to deliver a sequence of initial alignment laser pulses to the target tissue location; a monitor to monitor images of the target tissue location and photodisruption byproduct caused by the initial alignment laser pulses to obtain a location of the photodisruption byproduct relative to the target tissue location; and a laser control unit that controls a power level of the pulsed laser beam to carry surgical laser pulses at a surgical pulse energy level different from the initial alignment laser pulses and operates the beam control optical module, based on monitored images of the target tissue and the photodisruption byproduct from the monitor, to adjust a position of the pulsed laser beam at the surgical pulse energy level to place the location of photodisruption byproduct at a desired location.

In another aspect, a method for performing laser surgery by using an imaging-guided laser surgical system includes using an applanation plate in the system to engage to and to hold a target tissue under surgery in position; sequentially or simultaneously directing a surgical laser beam of laser pulses from a laser in the system and an optical probe beam from an optical coherence tomography (OCT) module in the system to the patient interface into the target tissue; controlling the surgical laser beam to perform laser surgery in the target tissue; operating the OCT module to obtain OCT images inside the target tissue from light of the optical probe beam returning from the target tissue; and applying position information in the obtained OCT images in focusing and scanning of the surgical laser beam to dynamically adjust the focusing and scanning of the surgical laser beam in the target tissue before or during surgery.

In another aspect, a method for performing laser surgery by using an imaging-guided laser surgical system includes using an applanation plate in the system, to hold a calibration sample material during a calibration process before performing a surgery; directing a surgical laser beam of laser pulses from a laser in the system to the patient interface into the calibration sample material to burn reference marks at selected three dimensional reference locations; directing an optical probe beam from an optical coherence tomography (OCT) module in the system to the patient interface into the calibration sample material to capture OCT images of the burnt reference marks; establishing a relationship between positioning coordinates of the OCT module and the burnt reference marks; after the establishing the relationship, using a patient interface in the system to engage to and to hold a target tissue under surgery in position; simultaneously or sequentially directing the surgical laser beam of laser pulses and the optical probe beam to the patient interface into the target tissue; controlling the surgical laser beam to perform laser surgery in the target tissue; operating the OCT module to obtain OCT images inside the target tissue from light of the optical probe beam returning from the target tissue; and applying position information in the obtained OCT images and the established relationship in focusing and scanning of the surgical laser beam to dynamically adjust the focusing and scanning of the surgical laser beam in the target tissue before or during surgery.

In another aspect, a laser system for performing laser surgery on the eye includes a control system; a laser source emitting a laser beam for surgically affecting the tissue of an eye under a control of the control system; an optical coherence tomography (OCT) imaging system a control of the control system to produce a probe light beam that optically gathers information on an internal structure of the eye; an attachment mechanism structured to fix the surface of the eye in position and to provide reference in three dimensional space relative to the OCT imaging system; a mechanism to supply the control system with positional information on the internal structure of the eye derived from the OCT imaging system; and an optical unit that focuses the laser beam controlled by the control system into the eye for surgical treatment.

In another aspect, An imaging-guided laser surgical system includes a surgical laser that produces a surgical laser beam of surgical laser pulses that cause surgical changes in a target tissue under surgery; a patient interface mount that engages a patient interface in contact with the target tissue to hold the target tissue in position; a laser beam delivery module located between the surgical laser and the patient interface and configured to direct the surgical laser beam to the target tissue through the patient interface, the laser beam delivery module operable to scan the surgical laser beam in the target tissue along a predetermined surgical pattern; a laser control module that controls operation of the surgical laser and controls the laser beam delivery module to produce the predetermined surgical pattern; and an optical coherence tomography (OCT) module positioned relative to the patient interface to have a known spatial relation with respect to the patient interface and the target issue fixed to the patient interface. The OCT module is configured to direct an optical probe beam to the target tissue and receive returned probe light of the optical probe beam from the target tissue to capture OCT images of the target tissue while the surgical laser beam is being directed to the target tissue to perform an surgical operation so that the optical probe beam and the surgical laser beam are simultaneously present in the target tissue, the OCT module in communication with the laser control module to send information of the captured OCT images to the laser control module. The laser control module responds to the information of the captured OCT images to operate the laser beam delivery module in focusing and scanning of the surgical laser beam and adjusts the focusing and scanning of the surgical laser beam in the target tissue based on positioning information in the captured OCT images.

In another aspect, a laser system includes a pulse laser to produce a laser beam of laser pulses; an optics module to receive the laser beam and to focus and direct the laser beam onto a target tissue to cause photodisruption in the target tissue; an applanation plate operable to be in contact with the target tissue to produce an interface and to transmit laser pulses to the target and reflected light or sound from the target through the interface; an imaging device to capture reflected light from the target to create an image of the target tissue; and a system control module to process imaging information on the captured images from the image device and to control the optics module to adjust the laser beam focus to the target tissue.

In another aspect, a laser system includes a pulse laser to produce a laser beam of laser pulses; an optics module to focus and direct the laser beam onto a target tissue to cause photodisruption in the target tissue; an applanation plate operable to be in contact with the target tissue to produce an interface and to transmit laser pulses to the target and reflected light or sound from the target through the interface; an imaging device to capture an image of the target tissue and an image of the photodisruption byproduct generated in the target tissue by the photodisruption; and a system control module to process imaging information on the captures images from the image device to obtain an offset in position between the image of the photodisruption byproduct and a targeted position in the target tissue, wherein the system control module operates to control the optics module to adjust the laser beam to reduce the offset in subsequent laser pulses.

In another aspect, a method for targeting a pulsed laser beam to a target tissue in laser surgery includes monitoring image of target tissue of a body part and image of a reference on the body part to aim the pulsed laser beam at the target tissue; and monitoring images of photodisruption byproduct and the target tissue to adjust the pulsed laser beam to overlap the location of the photodisruption byproduct with the target tissue.

In another aspect, a method for targeting a pulsed laser beam to a target tissue in laser surgery includes aiming a pulsed laser beam at a target tissue location within target tissue to deliver a sequence of initial alignment laser pulses to the target tissue location; monitoring images of the target tissue location and photodisruption byproduct caused by the initial alignment laser pulses to obtain a location of the photodisruption byproduct relative to the target tissue location; determining a location of photodisruption byproduct caused by surgical laser pulses at a surgical pulse energy level different from the initial alignment laser pulses when the pulsed laser beam of the surgical laser pulses is placed at the target tissue location; controlling the pulsed laser beam to carry surgical laser pulses at the surgical pulse energy level; adjusting a position of the pulsed laser beam at the surgical pulse energy level to place the location of photodisruption byproduct at the determined location; and, while monitoring images of the target tissue and the photodisruption byproduct, continuing to adjust position of the pulsed laser beam at the surgical pulse energy level to place the location of photodisruption byproduct at a respective determined location when moving the pulsed laser beam to a new target tissue location within the target tissue.

In yet another aspect, a laser surgical system includes a pulsed laser to produce a pulsed laser beam; a beam control optical module that directs the pulsed laser beam at a target tissue location within target tissue to deliver a sequence of initial alignment laser pulses to the target tissue location; a monitor to monitor images of the target tissue location and photodisruption byproduct caused by the initial alignment laser pulses to obtain a location of the photodisruption byproduct relative to the target tissue location; and a laser control unit that controls a power level of the pulsed laser beam to carry surgical laser pulses at a surgical pulse energy level different from the initial alignment laser pulses and operates the beam control optical module, based on monitored images of the target tissue and the photodisruption byproduct from the monitor, to adjust a position of the pulsed laser beam at the surgical pulse energy level to place the location of photodisruption byproduct at a desired location.

These and other aspects and various implementations of techniques, apparatus and systems for laser surgery are described in detail in the drawings, the description and the claims.

BRIEF DESCRIPTION OF THE DRAWINGS

FIGS. 17A and 17B show two operation modes of an exemplary imaging-guided laser surgical system that captures images of laser-induced photodisruption byproduct and the target issue to guide laser alignment.

DETAILED DESCRIPTION

Figure 1:
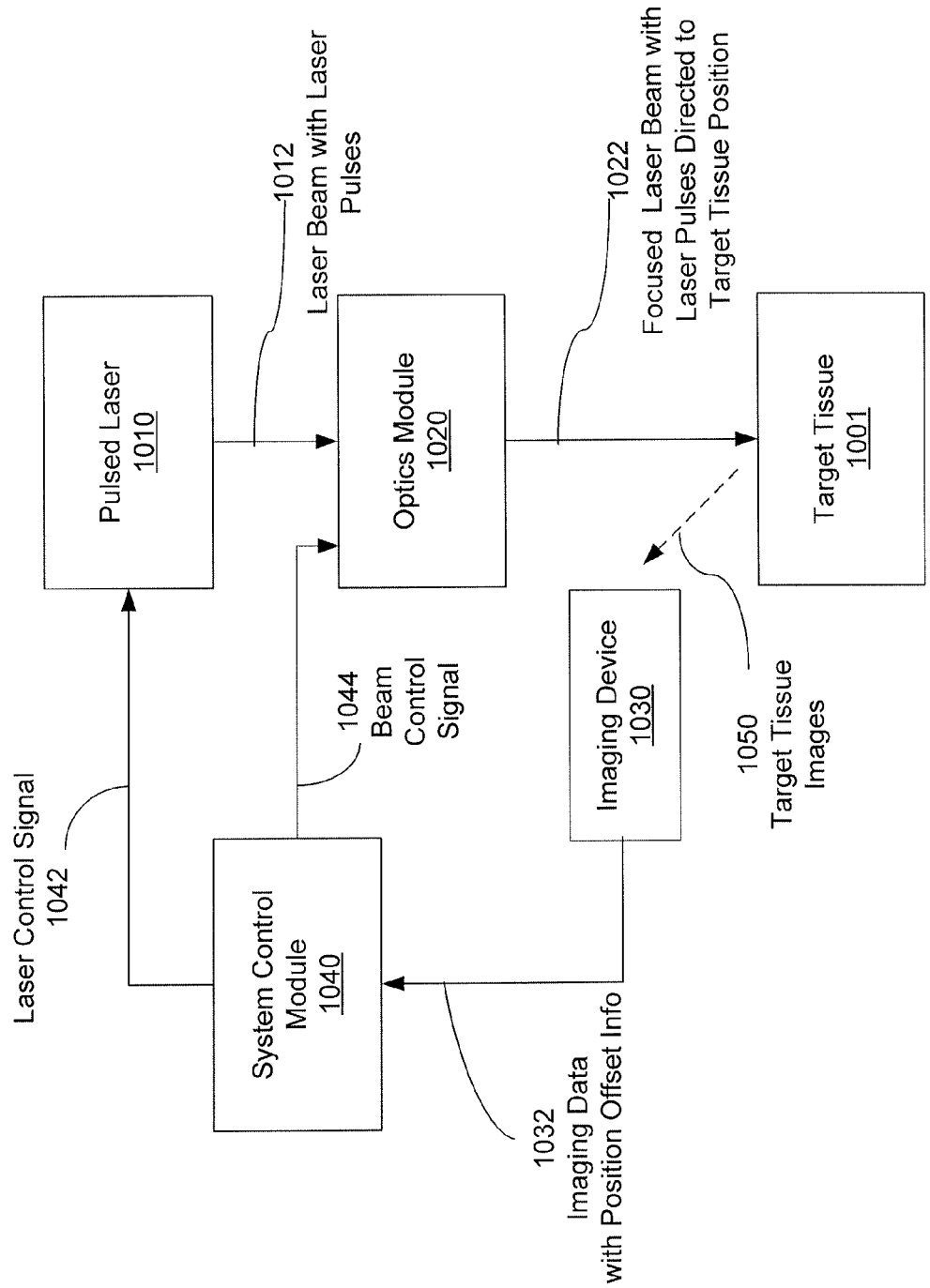
FIG. 1 shows an example of an imaging-guided laser surgical system in which an imaging module is provided to provide imaging of a target to the laser control.

One important aspect of laser surgical procedures is precise control and aiming of a laser beam, e.g., the beam position and beam focusing. Laser surgery systems can be designed to include laser control and aiming tools to precisely target laser pulses to a particular target inside the tissue. In various nanosecond photodisruptive laser surgical systems, such as the Nd:YAG laser systems, the required level of targeting precision is relatively low. This is in part because the laser energy used is relatively high and thus the affected tissue area is also relatively large, often covering an impacted area with a dimension in the hundreds of microns. The time between laser pulses in such systems tend to be long and manual controlled targeting is feasible and is commonly used. One example of such manual targeting mechanisms is a biomicroscope to visualize the target tissue in combination with a secondary laser source used as an aiming beam. The surgeon manually moves the focus of a laser focusing lens, usually with a joystick control, which is parfocal (with or without an offset) with their image through the microscope, so that the surgical beam or aiming beam is in best focus on the intended target.

Such techniques designed for use with low repetition rate laser surgical systems may be difficult to use with high repetition rate lasers operating at thousands of shots per second and relatively low energy per pulse. In surgical operations with high repetition rate lasers, much higher precision may be required due to the small effects of each single laser pulse and much higher positioning speed may be required due to the need to deliver thousands of pulses to new treatment areas very quickly.

Examples of high repetition rate pulsed lasers for laser surgical systems include pulsed lasers at a pulse repetition rate of thousands of shots per second or higher with relatively low energy per pulse. Such lasers use relatively low energy per pulse to localize the tissue effect caused by laser-induced photodisruption, e.g., the impacted tissue area by photodisruption on the order of microns or tens of microns. This localized tissue effect can improve the precision of the laser surgery and can be desirable in certain surgical procedures such as laser eye surgery. In one example of such surgery, placement of many hundred, thousands or millions of contiguous, nearly contiguous or pulses separated by known distances, can be used to achieve certain desired surgical effects, such as tissue incisions, separations or fragmentation.

Various surgical procedures using high repetition rate photodisruptive laser surgical systems with shorter laser pulse durations may require high precision in positioning each pulse in the target tissue under surgery both in an absolute position with respect to a target location on the target tissue and a relative position with respect to preceding pulses. For example, in some cases, laser pulses may be required to be delivered next to each other with an accuracy of a few microns within the time between pulses, which can be on the order of microseconds. Because the time between two sequential pulses is short and the precision requirement for the pulse alignment is high, manual targeting as used in low repetition rate pulsed laser systems may be no longer adequate or feasible.

One technique to facilitate and control precise, high speed positioning requirement for delivery of laser pulses into the tissue is attaching a applanation plate made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. Contact lenses can be designed for various applications and targets inside the eye and other tissues, including ones that are disposable or reusable. The contact glass or applanation plate on the surface of the target tissue can be used as a reference plate relative to which laser pulses are focused through the adjustment of focusing elements within the laser delivery system. This use of a contact glass or applanation plate provides better control of the optical qualities of the tissue surface and thus allow laser pulses to be accurately placed at a high speed at a desired location (interaction point) in the target tissue relative to the applanation plate with little optical distortion of the laser pulses.

One way for implementing an applanation plate on an eye is to use the applanation plate to provide a positional reference for delivering the laser pulses into a target tissue in the eye. This use of the applanation plate as a positional reference can be based on the known desired location of laser pulse focus in the target with sufficient accuracy prior to firing the laser pulses and that the relative positions of the reference plate and the individual internal tissue target must remain constant during laser firing. In addition, this method can require the focusing of the laser pulse to the desired location to be predictable and repeatable between eyes or in different regions within the same eye. In practical systems, it can be difficult to use the applanation plate as a positional reference to precisely localize laser pulses intraocularly because the above conditions may not be met in practical systems.

For example, if the crystalline lens is the surgical target, the precise distance from the reference plate on the surface of the eye to the target tends to vary due to the presence of a collapsible structures, such as the cornea itself, the anterior chamber, and the iris. Not only is their considerable variability in the distance between the applanated cornea and the lens between individual eyes, but there can also be variation within the same eye depending on the specific surgical and applanation technique used by the surgeon. In addition, there can be movement of the targeted lens tissue relative to the applanated surface during the firing of the thousands of laser pulses required for achieving the surgical effect, further complicating the accurate delivery of pulses. In addition, structure within the eye may move due to the build-up of photodisruptive byproducts, such as cavitation bubbles. For example, laser pulses delivered to the crystalline lens can cause the lens capsule to bulge forward, requiring adjustment to target this tissue for subsequent placement of laser pulses. Furthermore, it can be difficult to use computer models and simulations to predict, with sufficient accuracy, the actual location of target tissues after the applanation plate is removed and to adjust placement of laser pulses to achieve the desired localization without applanation in part because of the highly variable nature of applanation effects, which can depend on factors particular to the individual cornea or eye, and the specific surgical and applanation technique used by a surgeon.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption is a nonlinear optical process in the tissue material and can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. In addition, it may be necessary to adjust the energy in each pulse to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses.

Thus, in surgical procedures in which non superficial structures are targeted, the use of a superficial applanation plate based on a positional reference provided by the applanation plate may be insufficient to achieve precise laser pulse localization in internal tissue targets. The use of the applanation plate as the reference for guiding laser delivery may require measurements of the thickness and plate position of the applanation plate with high accuracy because the deviation from nominal is directly translated into a depth precision error. High precision applanation lenses can be costly, especially for single use disposable applanation plates.

The techniques, apparatus and systems described in this document can be implemented in ways that provide a targeting mechanism to deliver short laser pulses through an applanation plate to a desired localization inside the eye with precision and at a high speed without requiring the known desired location of laser pulse focus in the target with sufficient accuracy prior to firing the laser pulses and without requiring that the relative positions of the reference plate and the individual internal tissue target remain constant during laser firing. As such, the present techniques, apparatus and systems can be used for various surgical procedures where physical conditions of the target tissue under surgery tend to vary and are difficult to control and the dimension of the applanation lens tends to vary from one lens to another. The present techniques, apparatus and systems may also be used for other surgical targets where distortion or movement of the surgical target relative to the surface of the structure is present or non-linear optical effects make precise targeting problematic. Examples for such surgical targets different from the eye include the heart, deeper tissue in the skin and others.

The present techniques, apparatus and systems can be implemented in ways that maintain the benefits provided by an applanation plate, including, for example, control of the surface shape and hydration, as well as reductions in optical distortion, while providing for the precise localization of photodisruption to internal structures of the applanated surface. This can be accomplished through the use of an integrated imaging device to localize the target tissue relative to the focusing optics of the delivery system. The exact type of imaging device and method can vary and may depend on the specific nature of the target and the required level of precision.

An applanation lens may be implemented with another mechanism to fix the eye to prevent translational and rotational movement of the eye. Examples of such fixation devices include the use of a suction ring. Such fixation mechanism can also lead to unwanted distortion or movement of the surgical target. The present techniques, apparatus and systems can be implemented to provide, for high repetition rate laser surgical systems that utilize an applanation plate and/or fixation means for non-superficial surgical targets, a targeting mechanism to provide intraoperative imaging to monitor such distortion and movement of the surgical target.

Specific examples of laser surgical techniques, apparatus and systems are described below to use an optical imaging module to capture images of a target tissue to obtain positioning information of the target tissue, e.g., before and during a surgical procedure. Such obtained positioning information can be used to control the positioning and focusing of the surgical laser beam in the target tissue to provide accurate control of the placement of the surgical laser pulses in high repetition rate laser systems. In one implementation, during a surgical procedure, the images obtained by the optical imaging module can be used to dynamically control the position and focus of the surgical laser beam. In addition, lower energy and shot laser pulses tend to be sensitive to optical distortions, such a laser surgical system can implement an applanation plate with a flat or curved interface attaching to the target tissue to provide a controlled and stable optical interface between the target tissue and the surgical laser system and to mitigate and control optical aberrations at the tissue surface.

As an example, FIG. 1 shows a laser surgical system based on optical imaging and applanation. This system includes a pulsed laser 1010 to produce a surgical laser beam 1012 of laser pulses, and an optics module 1020 to receive the surgical laser beam 1012 and to focus and direct the focused surgical laser beam 1022 onto a target tissue 1001, such as an eye, to cause photodisruption in the target tissue 1001. An applanation plate can be provided to be in contact with the target tissue 1001 to produce an interface for transmitting laser pulses to the target tissue 1001 and light coming from the target tissue 1001 through the interface. Notably, an optical imaging device 1030 is provided to capture light 1050 carrying target tissue images 1050 or imaging information from the target tissue 1001 to create an image of the target tissue 1001. The imaging signal 1032 from the imaging device 1030 is sent to a system control module 1040. The system control module 1040 operates to process the captured images from the image device 1030 and to control the optics module 1020 to adjust the position and focus of the surgical laser beam 1022 at the target tissue 101 based on information from the captured images. The optics module 120 can include one or more lenses and may further include one or more reflectors. A control actuator can be included in the optics module 1020 to adjust the focusing and the beam direction in response to a beam control signal 1044 from the system control module 1040. The control module 1040 can also control the pulsed laser 1010 via a laser control signal 1042.

The optical imaging device 1030 may be implemented to produce an optical imaging beam that is separate from the surgical laser beam 1022 to probe the target tissue 1001 and the returned light of the optical imaging beam is captured by the optical imaging device 1030 to obtain the images of the target tissue 1001. One example of such an optical imaging device 1030 is an optical coherence tomography (OCT) imaging module which uses two imaging beams, one probe beam directed to the target tissue 1001 thought the applanation plate and another reference beam in a reference optical path, to optically interfere with each other to obtain images of the target tissue 1001. In other implementations, the optical imaging device 1030 can use scattered or reflected light from the target tissue 1001 to capture images without sending a designated optical imaging beam to the target tissue 1001. For example, the imaging device 1030 can be a sensing array of sensing elements such as CCD or CMS sensors. For example, the images of photodisruption byproduct produced by the surgical laser beam 1022 may be captured by the optical imaging device 1030 for controlling the focusing and positioning of the surgical laser beam 1022. When the optical imaging device 1030 is designed to guide surgical laser beam alignment using the image of the photodisruption byproduct, the optical imaging device 1030 captures images of the photodisruption byproduct such as the laser-induced bubbles or cavities. The imaging device 1030 may also be an ultrasound imaging device to capture images based on acoustic images.

The system control module 1040 processes image data from the imaging device 1030 that includes the position offset information for the photodisruption byproduct from the target tissue position in the target tissue 1001. Based on the information obtained from the image, the beam control signal 1044 is generated to control the optics module 1020 which adjusts the laser beam 1022. A digital processing unit can be included in the system control module 1040 to perform various data processing for the laser alignment.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

The applanation plate in the present systems is provided to facilitate and control precise, high speed positioning requirement for delivery of laser pulses into the tissue. Such an applanation plate can be made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. A number of contact lenses have been designed for various applications and targets inside the eye and other tissues, including ones that are disposable or reusable. The contact glass or applanation plate on the surface of the target tissue is used as a reference plate relative to which laser pulses are focused through the adjustment of focusing elements within the laser delivery system relative. Inherent in such an approach are the additional benefits afforded by the contact glass or applanation plate described previously, including control of the optical qualities of the tissue surface. Accordingly, laser pulses can be accurately placed at a high speed at a desired location (interaction point) in the target tissue relative to the applanation plate with little optical distortion of the laser pulses.

The optical imaging device 1030 in FIG. 1 captures images of the target tissue 1001 via the applanation plate. The control module 1040 processes the captured images to extract position information from the captured images and uses the extracted position information as a position reference or guide to control the position and focus of the surgical laser beam 1022. This imaging-guided laser surgery can be implemented without relying on the applanation plate as a position reference because the position of the applanation plate tends to change due to various factors as discussed above. Hence, although the applanation plate provides a desired optical interface for the surgical laser beam to enter the target tissue and to capture images of the target tissue, it may be difficult to use the applanation plate as a position reference to align and control the position and focus of the surgical laser beam for accurate delivery of laser pulses. The imaging-guided control of the position and focus of the surgical laser beam based on the imaging device 1030 and the control module 1040 allows the images of the target tissue 1001, e.g., images of inner structures of an eye, to be used as position references, without using the applanation plate to provide a position reference.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. The energy of the laser pulses may be adjusted to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses. In this regard, the direct images obtained from the target issue by the imaging device 1030 can be used to monitor the actual position of the surgical laser beam 1022 which reflects the combined effects of nonlinear optical effects in the target tissue and provide position references for control of the beam position and beam focus.

The techniques, apparatus and systems described here can be used in combination of an applanation plate to provide control of the surface shape and hydration, to reduce optical distortion, and provide for precise localization of photodisruption to internal structures through the applanated surface. The imaging-guided control of the beam position and focus described here can be applied to surgical systems and procedures that use means other than applanation plates to fix the eye, including the use of a suction ring which can lead to distortion or movement of the surgical target.

The following sections first describe examples of techniques, apparatus and systems for automated imaging-guided laser surgery based on varying degrees of integration of imaging functions into the laser control part of the systems. An optical or other modality imaging module, such as an OCT imaging module, can be used to direct a probe light or other type of beam to capture images of a target tissue, e.g., structures inside an eye. A surgical laser beam of laser pulses such as femtosecond or picosecond laser pulses can be guided by position information in the captured images to control the focusing and positioning of the surgical laser beam during the surgery. Both the surgical laser beam and the probe light beam can be sequentially or simultaneously directed to the target tissue during the surgery so that the surgical laser beam can be controlled based on the captured images to ensure precision and accuracy of the surgery.

Such imaging-guided laser surgery can be used to provide accurate and precise focusing and positioning of the surgical laser beam during the surgery because the beam control is based on images of the target tissue following applanation or fixation of the target tissue, either just before or nearly simultaneously with delivery of the surgical pulses. Notably, certain parameters of the target tissue such as the eye measured before the surgery may change during the surgery due to various factor such as preparation of the target tissue (e.g., fixating the eye to an applanation lens) and the alternation of the target tissue by the surgical operations. Therefore, measured parameters of the target tissue prior to such factors and/or the surgery may no longer reflect the physical conditions of the target tissue during the surgery. The present imaging-guided laser surgery can mitigate technical issues in connection with such changes for focusing and positioning the surgical laser beam before and during the surgery.

The present imaging-guided laser surgery may be effectively used for accurate surgical operations inside a target tissue. For example, when performing laser surgery inside the eye, laser light is focused inside the eye to achieve optical breakdown of the targeted tissue and such optical interactions can change the internal structure of the eye. For example, the crystalline lens can change its position, shape, thickness and diameter during accommodation, not only between prior measurement and surgery but also during surgery. Attaching the eye to the surgical instrument by mechanical means can change the shape of the eye in a not well defined way and further, the change can vary during surgery due to various factors, e.g., patient movement. Attaching means include fixating the eye with a suction ring and aplanating the eye with a flat or curved lens. These changes amount to as much as a few millimeters. Mechanically referencing and fixating the surface of the eye such as the anterior surface of the cornea or limbus does not work well when performing precision laser microsurgery inside the eye.

The post preparation or near simultaneous imaging in the present imaging-guided laser surgery can be used to establish three-dimensional positional references between the inside features of the eye and the surgical instrument in an environment where changes occur prior to and during surgery. The positional reference information provided by the imaging prior to applanation and/or fixation of the eye, or during the actual surgery reflects the effects of changes in the eye and thus provides an accurate guidance to focusing and positioning of the surgical laser beam. A system based on the present imaging-guided laser surgery can be configured to be simple in structure and cost efficient. For example, a portion of the optical components associated with guiding the surgical laser beam can be shared with optical components for guiding the probe light beam for imaging the target tissue to simplify the device structure and the optical alignment and calibration of the imaging and surgical light beams.

The imaging-guided laser surgical systems described below use the OCT imaging as an example of an imaging instrument and other non-OCT imaging devices may also be used to capture images for controlling the surgical lasers during the surgery. As illustrated in the examples below, integration of the imaging and surgical subsystems can be implemented to various degrees. In the simplest form without integrating hardware, the imaging and laser surgical subsystems are separated and can communicate to one another through interfaces. Such designs can provide flexibility in the designs of the two subsystems. Integration between the two subsystems, by some hardware components such as a patient interface, further expands the functionality by offering better registration of surgical area to the hardware components, more accurate calibration and may improve workflow. As the degree of integration between the two subsystems increases, such a system may be made increasingly cost-efficient and compact and system calibration will be further simplified and more stable over time. Examples for imaging-guided laser systems in FIGS. 2-10 are integrated at various degrees of integration.

One implementation of a present imaging-guided laser surgical system, for example, includes a surgical laser that produces a surgical laser beam of surgical laser pulses that cause surgical changes in a target tissue under surgery; a patient interface mount that engages a patient interface in contact with the target tissue to hold the target tissue in position; and a laser beam delivery module located between the surgical laser and the patient interface and configured to direct the surgical laser beam to the target tissue through the patient interface. This laser beam delivery module is operable to scan the surgical laser beam in the target tissue along a predetermined surgical pattern. This system also includes a laser control module that controls operation of the surgical laser and controls the laser beam delivery module to produce the predetermined surgical pattern and an OCT module positioned relative to the patient interface to have a known spatial relation with respect to the patient interface and the target issue fixed to the patient interface. The OCT module is configured to direct an optical probe beam to the target tissue and receive returned probe light of the optical probe beam from the target tissue to capture OCT images of the target tissue while the surgical laser beam is being directed to the target tissue to perform an surgical operation so that the optical probe beam and the surgical laser beam are simultaneously present in the target tissue. The OCT module is in communication with the laser control module to send information of the captured OCT images to the laser control module.

In addition, the laser control module in this particular system responds to the information of the captured OCT images to operate the laser beam delivery module in focusing and scanning of the surgical laser beam and adjusts the focusing and scanning of the surgical laser beam in the target tissue based on positioning information in the captured OCT images.

In some implementations, acquiring a complete image of a target tissue may not be necessary for registering the target to the surgical instrument and it may be sufficient to acquire a portion of the target tissue, e.g., a few points from the surgical region such as natural or artificial landmarks. For example, a rigid body has 6 degrees of freedom in 3D space and six independent points would be sufficient to define the rigid body. When the exact size of the surgical region is not known, additional points are needed to provide the positional reference. In this regard, several points can be used to determine the position and the curvature of the anterior and posterior surfaces, which are normally different, and the thickness and diameter of the crystalline lens of the human eye. Based on these data a body made up from two halves of ellipsoid bodies with given parameters can approximate and visualize a crystalline lens for practical purposes. In another implementation, information from the captured image may be combined with information from other sources, such as pre-operative measurements of lens thickness that are used as an input for the controller.

Figure 2:
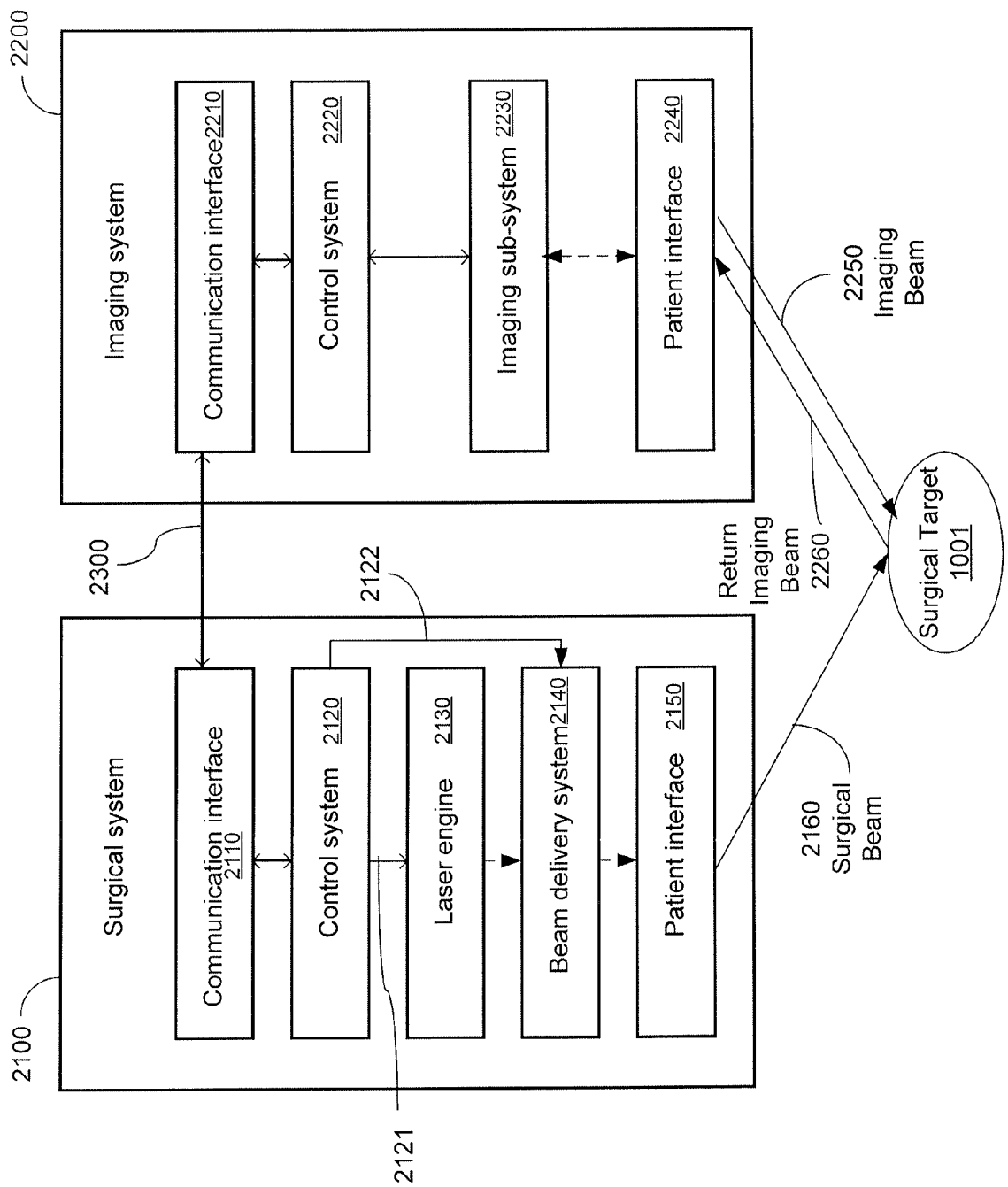
FIGS. 2-10 show examples of imaging-guided laser surgical systems with varying degrees of integration of a laser surgical system and an imaging system.

FIG. 2 shows one example of an imaging-guided laser surgical system with separated laser surgical system 2100 and imaging system 2200. The laser surgical system 2100 includes a laser engine 2130 with a surgical laser that produces a surgical laser beam 2160 of surgical laser pulses. A laser beam delivery module 2140 is provided to direct the surgical laser beam 2160 from the laser engine 2130 to the target tissue 1001 through a patient interface 2150 and is operable to scan the surgical laser beam 2160 in the target tissue 1001 along a predetermined surgical pattern. A laser control module 2120 is provided to control the operation of the surgical laser in the laser engine 2130 via a communication channel 2121 and controls the laser beam delivery module 2140 via a communication channel 2122 to produce the predetermined surgical pattern. A patient interface mount is provided to engage the patient interface 2150 in contact with the target tissue 1001 to hold the target tissue 1001 in position. The patient interface 2150 can be implemented to include a contact lens or applanation lens with a flat or curved surface to conformingly engage to the anterior surface of the eye and to hold the eye in position.

The imaging system 2200 in FIG. 2 can be an OCT module positioned relative to the patient interface 2150 of the surgical system 2100 to have a known spatial relation with respect to the patient interface 2150 and the target issue 1001 fixed to the patient interface 2150. This OCT module 2200 can be configured to have its own patient interface 2240 for interacting with the target tissue 1001. The imaging system 220 includes an imaging control module 2220 and an imaging sub-system 2230. The sub-system 2230 includes a light source for generating imaging beam 2250 for imaging the target 1001 and an imaging beam delivery module to direct the optical probe beam or imaging beam 2250 to the target tissue 1001 and receive returned probe light 2260 of the optical imaging beam 2250 from the target tissue 1001 to capture OCT images of the target tissue 1001. Both the optical imaging beam 2250 and the surgical beam 2160 can be simultaneously directed to the target tissue 1001 to allow for sequential or simultaneous imaging and surgical operation.

As illustrated in FIG. 2, communication interfaces 2110 and 2210 are provided in both the laser surgical system 2100 and the imaging system 2200 to facilitate the communications between the laser control by the laser control module 2120 and imaging by the imaging system 2200 so that the OCT module 2200 can send information of the captured OCT images to the laser control module 2120. The laser control module 2120 in this system responds to the information of the captured OCT images to operate the laser beam delivery module 2140 in focusing and scanning of the surgical laser beam 2160 and dynamically adjusts the focusing and scanning of the surgical laser beam 2160 in the target tissue 1001 based on positioning information in the captured OCT images. The integration between the laser surgical system 2100 and the imaging system 2200 is mainly through communication between the communication interfaces 2110 and 2210 at the software level.

In this and other examples, various subsystems or devices may also be integrated. For example, certain diagnostic instruments such as wavefront aberrometers, corneal topography measuring devices may be provided in the system, or pre-operative information from these devices can be utilized to augment intra-operative imaging.

Figure 3:
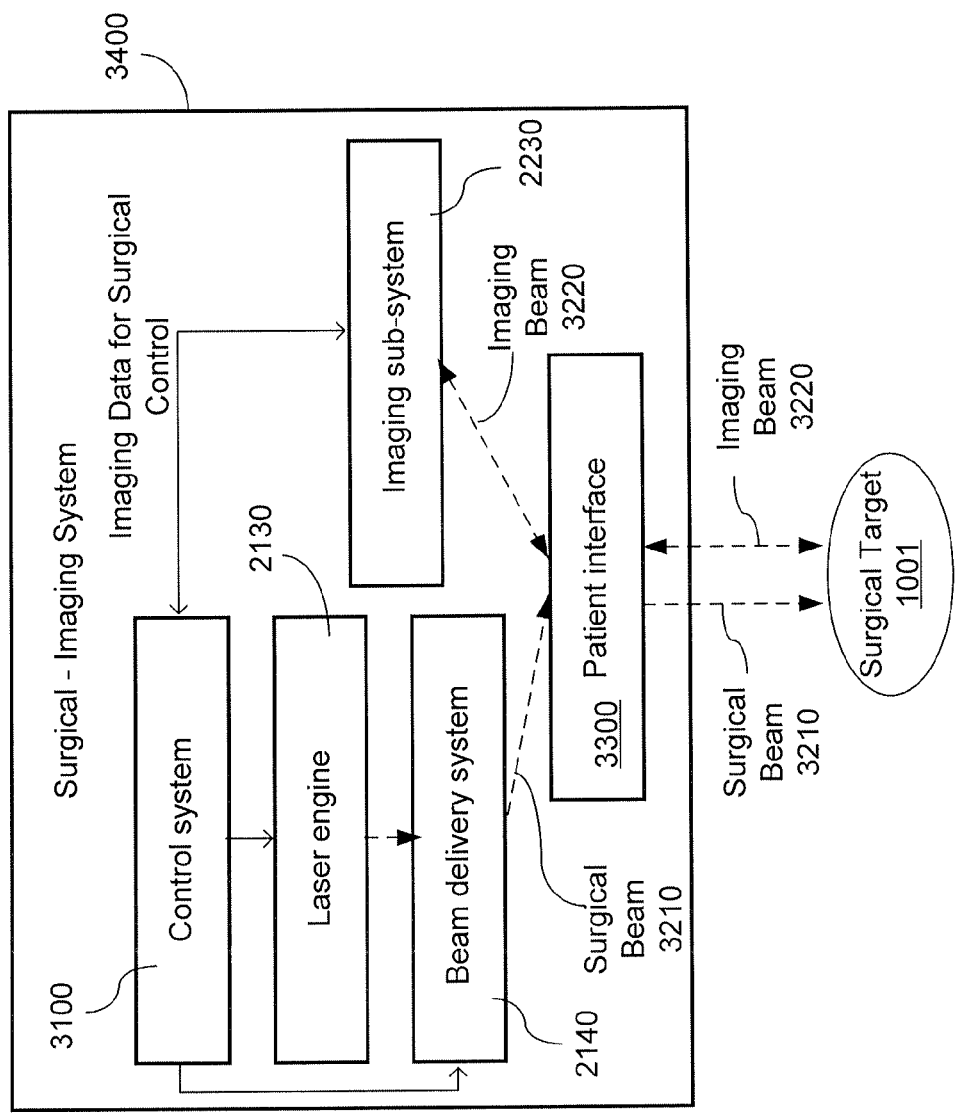

FIG. 3 shows an example of an imaging-guided laser surgical system with additional integration features. The imaging and surgical systems share a common patient interface 3300 which immobilizes target tissue 1001 (e.g., the eye) without having two separate patient interfaces as in FIG. 2. The surgical beam 3210 and the imaging beam 3220 are combined at the patient interface 330 and are directed to the target 1001 by the common patient interface 3300. In addition, a common control module 3100 is provided to control both the imaging sub-system 2230 and the surgical part (the laser engine 2130 and the beam delivery system 2140). This increased integration between imaging and surgical parts allows accurate calibration of the two subsystems and the stability of the position of the patient and surgical volume. A common housing 3400 is provided to enclose both the surgical and imaging subsystems. When the two systems are not integrated into a common housing, the common patient interface 3300 can be part of either the imaging or the surgical subsystem.

Figure 4:
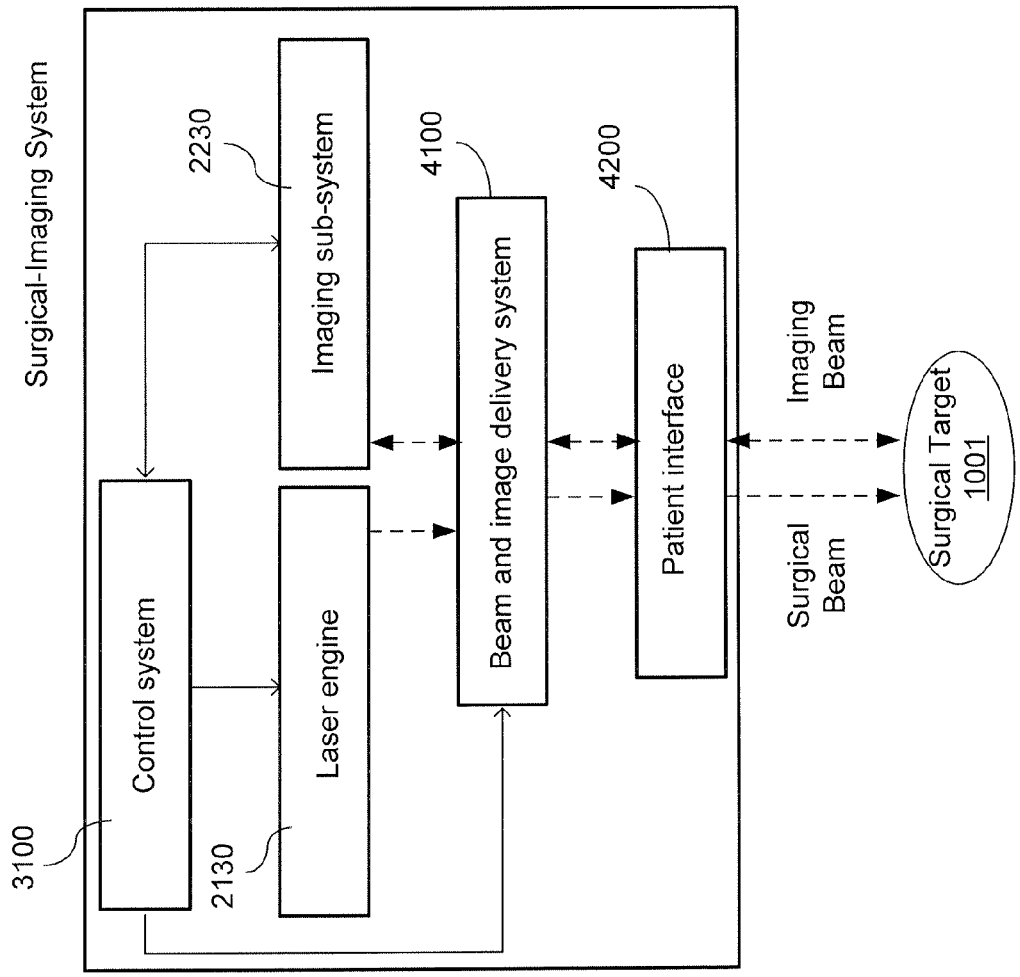

FIG. 4 shows an example of an imaging-guided laser surgical system where the laser surgical system and the imaging system share both a common beam delivery module 4100 and a common patient interface 4200. This integration further simplifies the system structure and system control operation.

In one implementation, the imaging system in the above and other examples can be an optical computed tomography (OCT) system and the laser surgical system is a femtosecond or picosecond laser based ophthalmic surgical system. In OCT, light from a low coherence, broadband light source such as a super luminescent diode is split into separate reference and signal beams. The signal beam is the imaging beam sent to the surgical target and the returned light of the imaging beam is collected and recombined coherently with the reference beam to form an interferometer. Scanning the signal beam perpendicularly to the optical axis of the optical train or the propagation direction of the light provides spatial resolution in the x-y direction while depth resolution comes from extracting differences between the path lengths of the reference arm and the returned signal beam in the signal arm of the interferometer. While the x-y scanner of different OCT implementations are essentially the same, comparing the path lengths and getting z-scan information can happen in different ways. In one implementation known as the time domain OCT, for example, the reference arm is continuously varied to change its path length while a photodetector detects interference modulation in the intensity of the recombined beam. In a different implementation, the reference arm is essentially static and the spectrum of the combined light is analyzed for interference. The Fourier transform of the spectrum of the combined beam provides spatial information on the scattering from the interior of the sample. This method is known as the spectral domain or Fourier OCT method. In a different implementation known as a frequency swept OCT (S. R. Chinn, et. Al. Opt. Lett. 22 (1997), a narrowband light source is used with its frequency swept rapidly across a spectral range. Interference between the reference and signal arms is detected by a fast detector and dynamic signal analyzer. An external cavity tuned diode laser or frequency tuned of frequency domain mode-locked (FDML) laser developed for this purpose (R. Huber et. Al. Opt. Express, 13, 2005) (S. H. Yun, IEEE J. of Sel. Q. El. 3(4) p. 1087-1096, 1997) can be used in these examples as a light source. A femtosecond laser used as a light source in an OCT system can have sufficient bandwidth and can provide additional benefits of increased signal to noise ratios.

The OCT imaging device in the systems in this document can be used to perform various imaging functions. For example, the OCT can be used to suppress complex conjugates resulting from the optical configuration of the system or the presence of the applanation plate, capture OCT images of selected locations inside the target tissue to provide three-dimensional positioning information for controlling focusing and scanning of the surgical laser beam inside the target tissue, or capture OCT images of selected locations on the surface of the target tissue or on the applanation plate to provide positioning registration for controlling changes in orientation that occur with positional changes of the target, such as from upright to supine. The OCT can be calibrated by a positioning registration process based on placement of marks or markers in one positional orientation of the target that can then be detected by the OCT module when the target is in another positional orientation. In other implementations, the OCT imaging system can be used to produce a probe light beam that is polarized to optically gather the information on the internal structure of the eye. The laser beam and the probe light beam may be polarized in different polarizations. The OCT can include a polarization control mechanism that controls the probe light used for said optical tomography to polarize in one polarization when traveling toward the eye and in a different polarization when traveling away from the eye. The polarization control mechanism can include, e.g., a wave-plate or a Faraday rotator.

The system in FIG. 4 is shown as a spectral OCT configuration and can be configured to share the focusing optics part of the beam delivery module between the surgical and the imaging systems. The main requirements for the optics are related to the operating wavelength, image quality, resolution, distortion etc. The laser surgical system can be a femtosecond laser system with a high numerical aperture system designed to achieve diffraction limited focal spot sizes, e.g., about 2 to 3 micrometers. Various femtosecond ophthalmic surgical lasers can operate at various wavelengths such as wavelengths of around 1.05 micrometer. The operating wavelength of the imaging device can be selected to be close to the laser wavelength so that the optics is chromatically compensated for both wavelengths. Such a system may include a third optical channel, a visual observation channel such as a surgical microscope, to provide an additional imaging device to capture images of the target tissue. If the optical path for this third optical channel shares optics with the surgical laser beam and the light of the OCT imaging device, the shared optics can be configured with chromatic compensation in the visible spectral band for the third optical channel and the spectral bands for the surgical laser beam and the OCT imaging beam.

Figure 5:
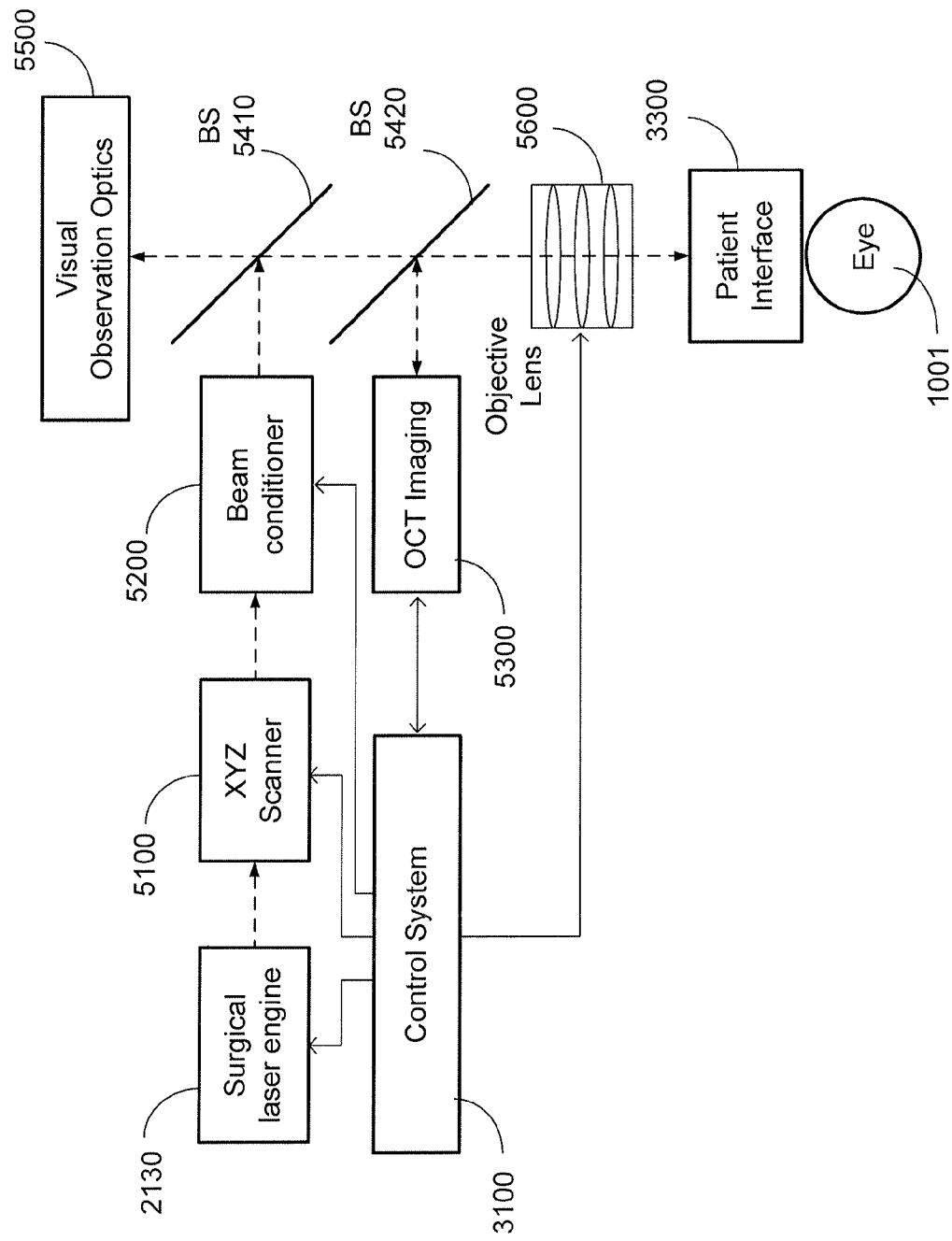

FIG. 5 shows a particular example of the design in FIG. 3 where the scanner 5100 for scanning the surgical laser beam and the beam conditioner 5200 for conditioning (collimating and focusing) the surgical laser beam are separate from the optics in the OCT imaging module 5300 for controlling the imaging beam for the OCT. The surgical and imaging systems share an objective lens 5600 module and the patient interface 3300. The objective lens 5600 directs and focuses both the surgical laser beam and the imaging beam to the patient interface 3300 and its focusing is controlled by the control module 3100. Two beam splitters 5410 and 5420 are provided to direct the surgical and imaging beams. The beam splitter 5420 is also used to direct the returned imaging beam back into the OCT imaging module 5300. Two beam splitters 5410 and 5420 also direct light from the target 1001 to a visual observation optics unit 5500 to provide direct view or image of the target 1001. The unit 5500 can be a lens imaging system for the surgeon to view the target 1001 or a camera to capture the image or video of the target 1001. Various beam splitters can be used, such as dichroic and polarization beam splitters, optical grating, holographic beam splitter or a combinations of these devices.

In some implementations, the optical components may be appropriately coated with antireflection coating for both the surgical and for the OCT wavelength to reduce glare from multiple surfaces of the optical beam path. Reflections would otherwise reduce the throughput of the system and reduce the signal to noise ratio by increasing background light in the OCT imaging unit. One way to reduce glare in the OCT is to rotate the polarization of the return light from the sample by wave-plate of Faraday isolator placed close to the target tissue and orient a polarizer in front of the OCT detector to preferentially detect light returned from the sample and suppress light scattered from the optical components.

In a laser surgical system, each of the surgical laser and the OCT system can have a beam scanner to cover the same surgical region in the target tissue. Hence, the beam scanning for the surgical laser beam and the beam scanning for the imaging beam can be integrated to share common scanning devices.

Figure 6:
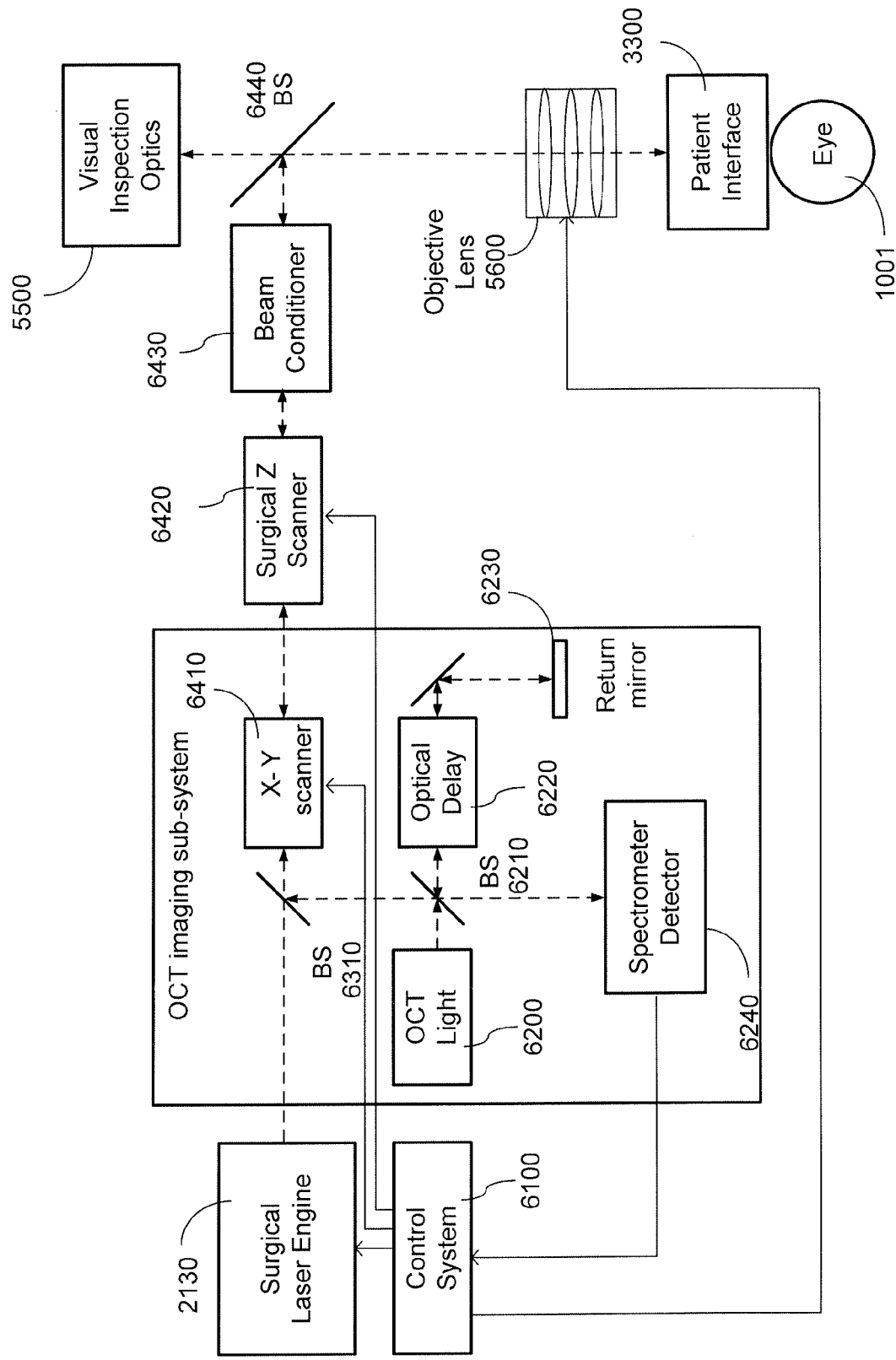

FIG. 6 shows an example of such a system in detail. In this implementation the x-y scanner 6410 and the z scanner 6420 are shared by both subsystems. A common control 6100 is provided to control the system operations for both surgical and imaging operations. The OCT sub-system includes an OCT light source 6200 that produce the imaging light that is split into an imaging beam and a reference beam by a beam splitter 6210. The imaging beam is combined with the surgical beam at the beam splitter 6310 to propagate along a common optical path leading to the target 1001. The scanners 6410 and 6420 and the beam conditioner unit 6430 are located downstream from the beam splitter 6310. A beam splitter 6440 is used to direct the imaging and surgical beams to the objective lens 5600 and the patient interface 3300.

In the OCT sub-system, the reference beam transmits through the beam splitter 6210 to an optical delay device 620 and is reflected by a return mirror 6230. The returned imaging beam from the target 1001 is directed back to the beam splitter 6310 which reflects at least a portion of the returned imaging beam to the beam splitter 6210 where the reflected reference beam and the returned imaging beam overlap and interfere with each other. A spectrometer detector 6240 is used to detect the interference and to produce OCT images of the target 1001. The OCT image information is sent to the control system 6100 for controlling the surgical laser engine 2130, the scanners 6410 and 6420 and the objective lens 5600 to control the surgical laser beam. In one implementation, the optical delay device 620 can be varied to change the optical delay to detect various depths in the target tissue 1001.

If the OCT system is a time domain system, the two subsystems use two different z-scanners because the two scanners operate in different ways. In this example, the z scanner of the surgical system operates by changing the divergence of the surgical beam in the beam conditioner unit without changing the path lengths of the beam in the surgical beam path. On the other hand, the time domain OCT scans the z-direction by physically changing the beam path by a variable delay or by moving the position of the reference beam return mirror. After calibration, the two z-scanners can be synchronized by the laser control module. The relationship between the two movements can be simplified to a linear or polynomial dependence, which the control module can handle or alternatively calibration points can define a look-up table to provide proper scaling. Spectral/Fourier domain and frequency swept source OCT devices have no z-scanner, the length of the reference arm is static. Besides reducing costs, cross calibration of the two systems will be relatively straightforward. There is no need to compensate for differences arising from image distortions in the focusing optics or from the differences of the scanners of the two systems since they are shared.

In practical implementations of the surgical systems, the focusing objective lens 5600 is slidably or movably mounted on a base and the weight of the objective lens is balanced to limit the force on the patient's eye. The patient interface 3300 can include an applanation lens attached to a patient interface mount. The patient interface mount is attached to a mounting unit, which holds the focusing objective lens. This mounting unit is designed to ensure a stable connection between the patient interface and the system in case of unavoidable movement of the patient and allows gentler docking of the patient interface onto the eye. Various implementations for the focusing objective lens can be used. This presence of an adjustable focusing objective lens can change the optical path length of the optical probe light as part of the optical interferometer for the OCT sub-system. Movement of the objective lens 5600 and patient interface 3300 can change the path length differences between the reference beam and the imaging signal beam of the OCT in an uncontrolled way and this may degrade the OCT depth information detected by the OCT. This would happen not only in time-domain but also in spectral/Fourier domain and frequency-swept OCT systems.

Figure 7:
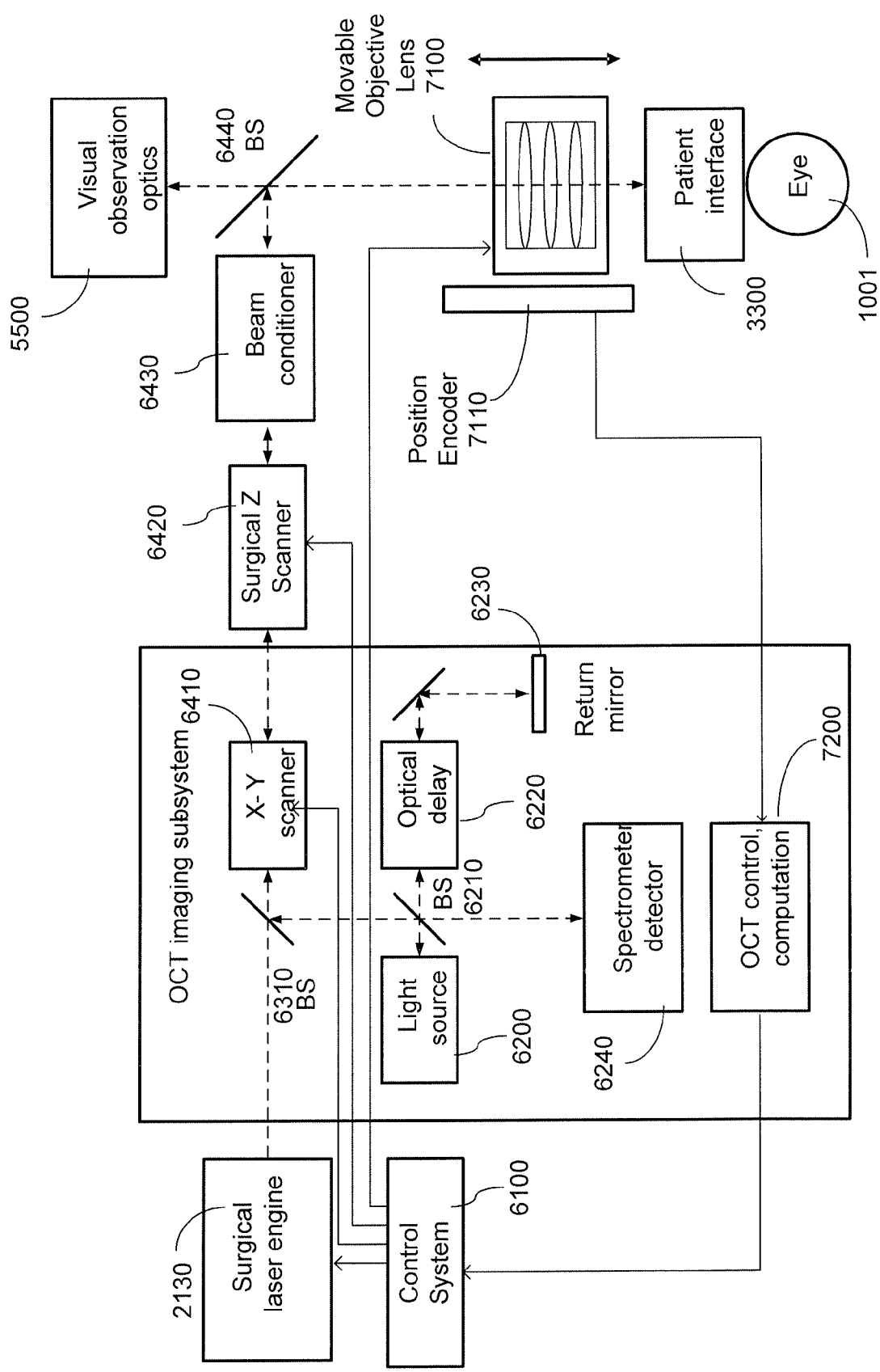
Figure 8:
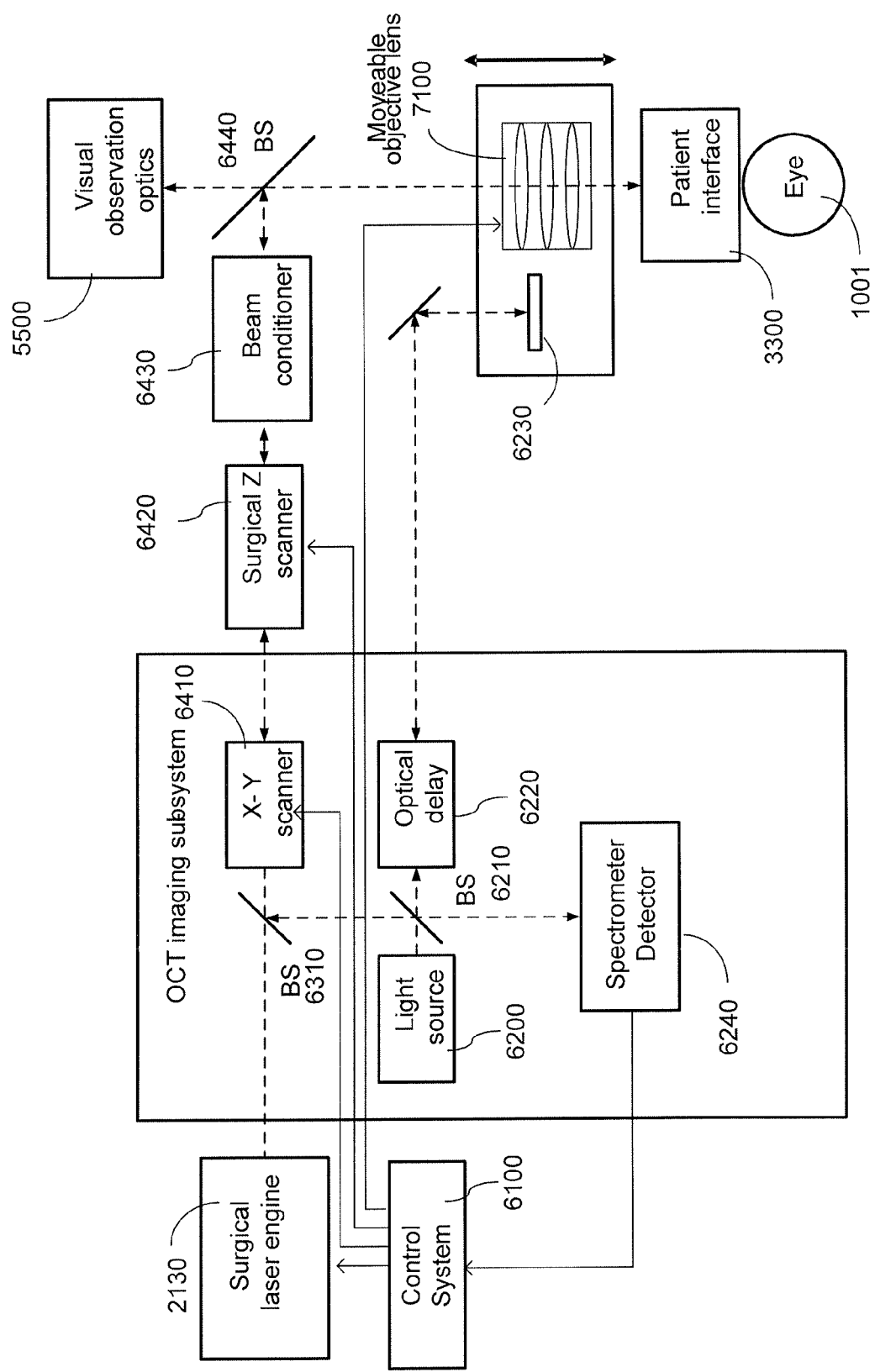

FIGS. 7 and 8 show exemplary imaging-guided laser surgical systems that address the technical issue associated with the adjustable focusing objective lens.

The system in FIG. 7 provides a position sensing device 7110 coupled to the movable focusing objective lens 7100 to measure the position of the objective lens 7100 on a slideable mount and communicates the measured position to a control module 7200 in the OCT system. The control system 6100 can control and move the position of the objective lens 7100 to adjust the optical path length traveled by the imaging signal beam for the OCT operation. A position encoder 7110 is coupled to the objective lens 7100 and configured to measure a position change of the objective lens 7100 relative to the applanation plate and the target tissue or relative to the OCT device. The measured position of the lens 7100 is then fed to the OCT control 7200. The control module 7200 in the OCT system applies an algorithm, when assembling a 3D image in processing the OCT data, to compensate for differences between the reference arm and the signal arm of the interferometer inside the OCT caused by the movement of the focusing objective lens 7100 relative to the patient interface 3300. The proper amount of the change in the position of the lens 7100 computed by the OCT control module 7200 is sent to the control 6100 which controls the lens 7100 to change its position.

FIG. 8 shows another exemplary system where the return mirror 6230 in the reference arm of the interferometer of the OCT system or at least one part in an optical path length delay assembly of the OCT system is rigidly attached to the movable focusing objective lens 7100 so the signal arm and the reference arm undergo the same amount of change in the optical path length when the objective lens 7100 moves. As such, the movement of the objective lens 7100 on the slide is automatically compensated for path-length differences in the OCT system without additional need for a computational compensation.

The above examples for imaging-guided laser surgical systems, the laser surgical system and the OCT system use different light sources. In an even more complete integration between the laser surgical system and the OCT system, a femtosecond surgical laser as a light source for the surgical laser beam can also be used as the light source for the OCT system.

Figure 9:
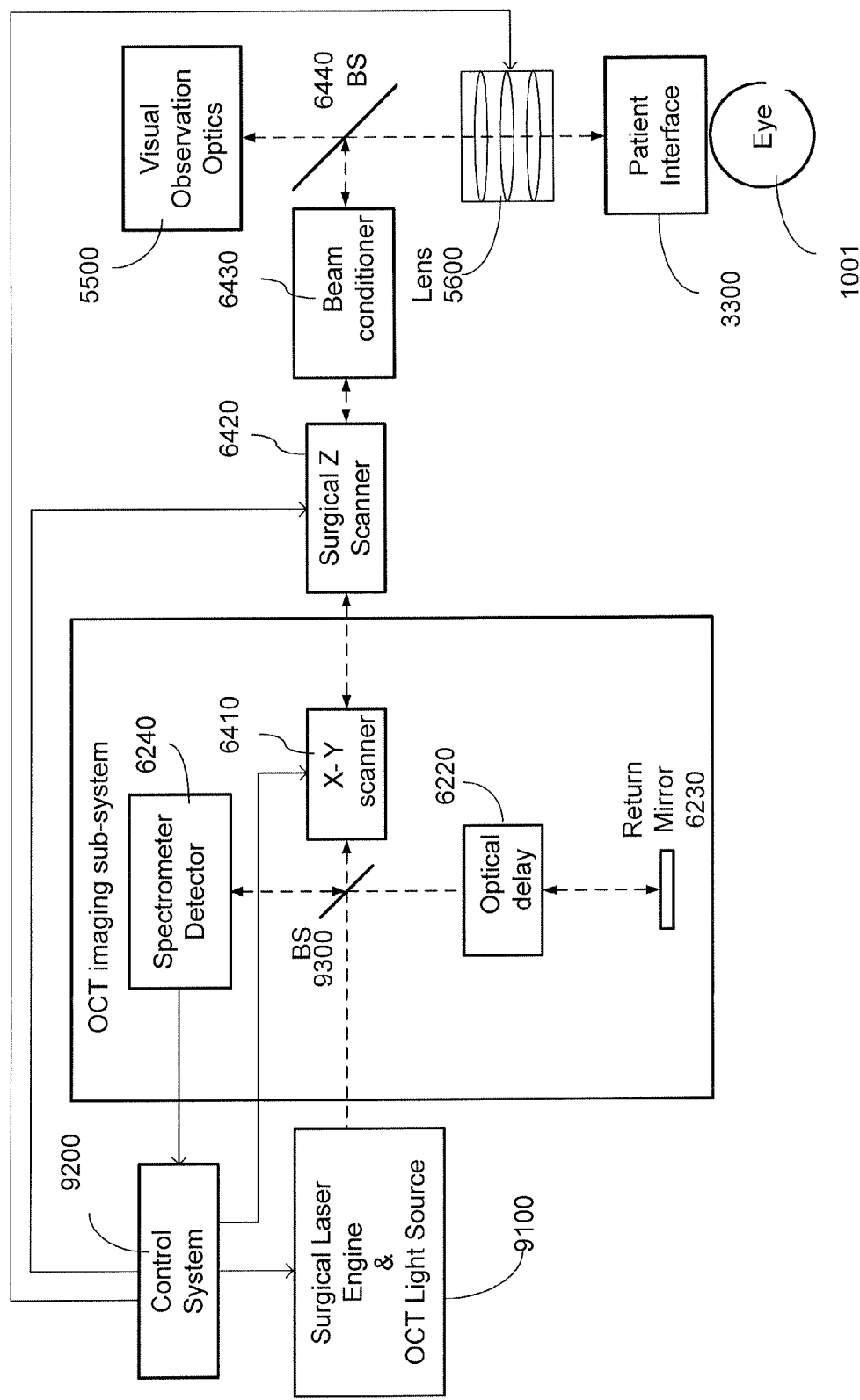

FIG. 9 shows an example where a femtosecond pulse laser in a light module 9100 is used to generate both the surgical laser beam for surgical operations and the probe light beam for OCT imaging. A beam splitter 9300 is provided to split the laser beam into a first beam as both the surgical laser beam and the signal beam for the OCT and a second beam as the reference beam for the OCT. The first beam is directed through an x-y scanner 6410 which scans the beam in the x and y directions perpendicular to the propagation direction of the first beam and a second scanner (z scanner) 6420 that changes the divergence of the beam to adjust the focusing of the first beam at the target tissue 1001. This first beam performs the surgical operations at the target tissue 1001 and a portion of this first beam is back scattered to the patient interface and is collected by the objective lens as the signal beam for the signal arm of the optical interferometer of the OCT system. This returned light is combined with the second beam that is reflected by a return mirror 6230 in the reference arm and is delayed by an adjustable optical delay element 6220 for an time-domain OCT to control the path difference between the signal and reference beams in imaging different depths of the target tissue 1001. The control system 9200 controls the system operations.

Surgical practice on the cornea has shown that a pulse duration of several hundred femtoseconds may be sufficient to achieve good surgical performance, while for OCT of a sufficient depth resolution broader spectral bandwidth generated by shorter pulses, e.g., below several tens of femtoseconds, are needed. In this context, the design of the OCT device dictates the duration of the pulses from the femtosecond surgical laser.

Figure 10:
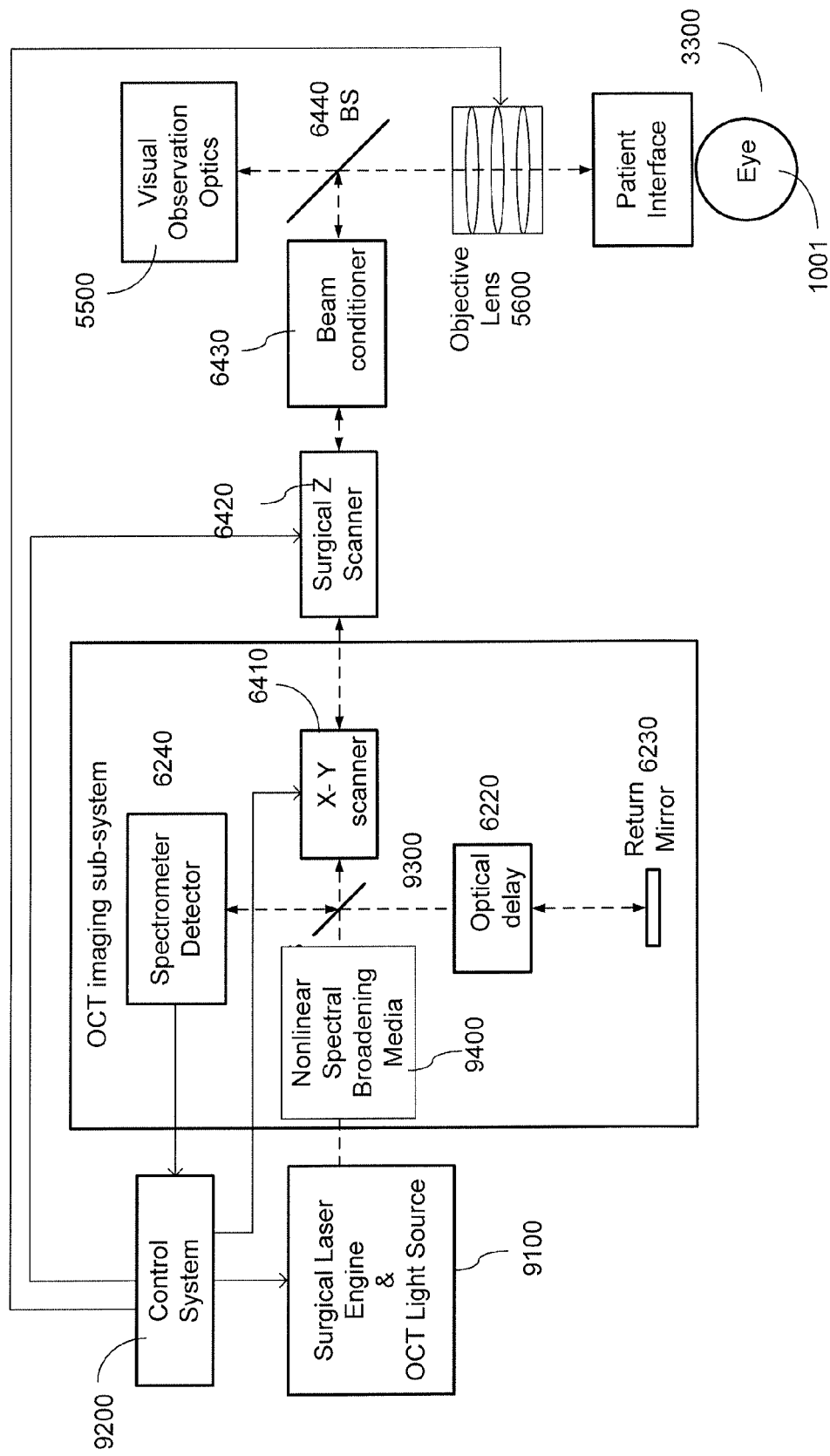

FIG. 10 shows another imaging-guided system that uses a single pulsed laser 9100 to produce the surgical light and the imaging light. A nonlinear spectral broadening media 9400 is placed in the output optical path of the femtosecond pulsed laser to use an optical non-linear process such as white light generation or spectral broadening to broaden the spectral bandwidth of the pulses from a laser source of relatively longer pulses, several hundred femtoseconds normally used in surgery. The media 9400 can be a fiber-optic material, for example. The light intensity requirements of the two systems are different and a mechanism to adjust beam intensities can be implemented to meet such requirements in the two systems. For example, beam steering mirrors, beam shutters or attenuators can be provided in the optical paths of the two systems to properly control the presence and intensity of the beam when taking an OCT image or performing surgery in order to protect the patient and sensitive instruments from excessive light intensity.

Figure 11:
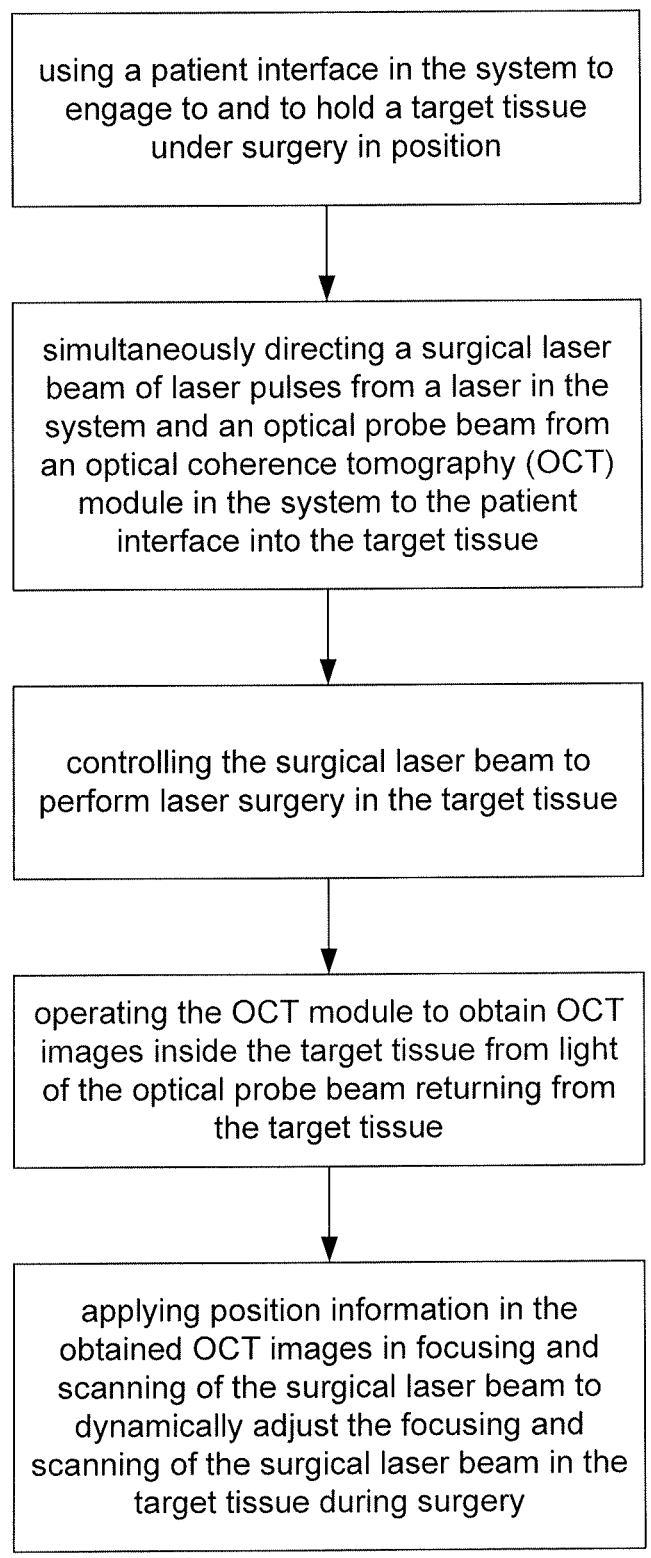
FIG. 11 shows an example of a method for performing laser surgery by suing an imaging-guided laser surgical system.

In operation, the above examples in FIGS. 2-10 can be used to perform imaging-guided laser surgery. FIG. 11 shows one example of a method for performing laser surgery by using an imaging-guided laser surgical system. This method uses a patient interface in the system to engage to and to hold a target tissue under surgery in position and simultaneously directs a surgical laser beam of laser pulses from a laser in the system and an optical probe beam from the OCT module in the system to the patient interface into the target tissue. The surgical laser beam is controlled to perform laser surgery in the target tissue and the OCT module is operated to obtain OCT images inside the target tissue from light of the optical probe beam returning from the target tissue. The position information in the obtained OCT images is applied in focusing and scanning of the surgical laser beam to adjust the focusing and scanning of the surgical laser beam in the target tissue before or during surgery.

Figure 12:
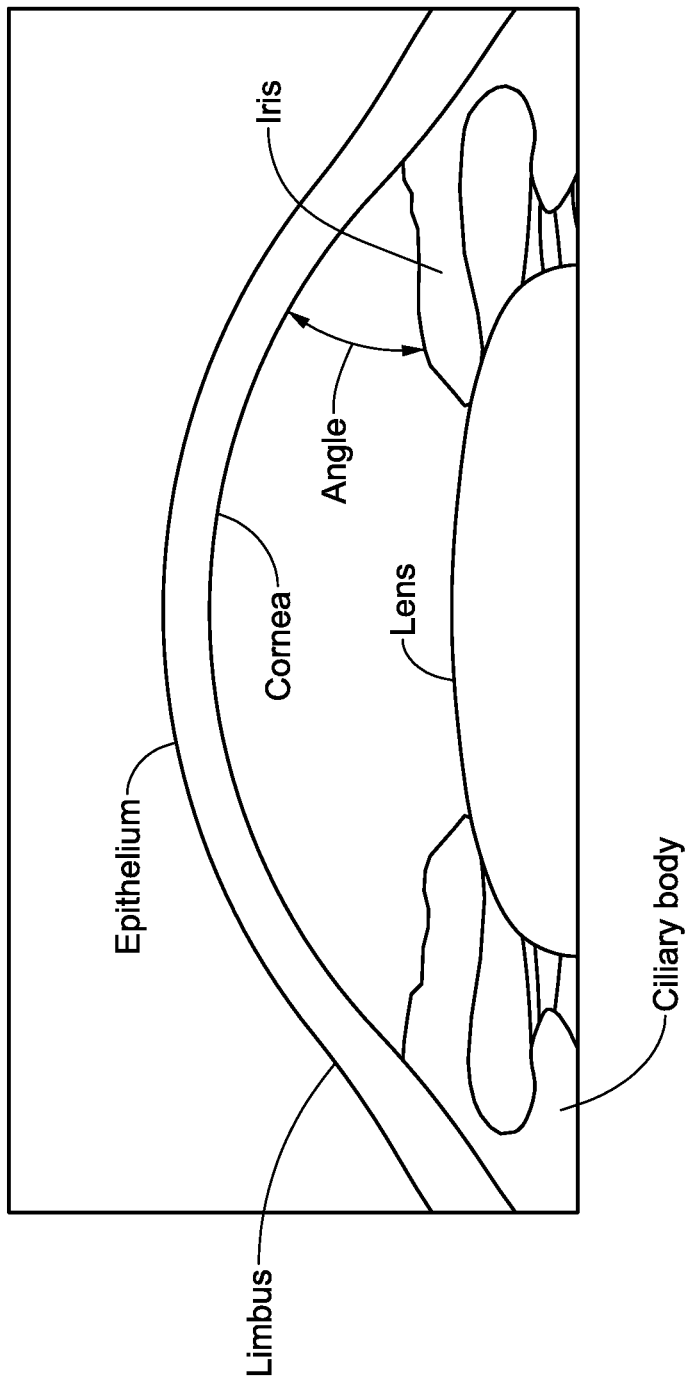
FIG. 12 shows an example of an image of an eye from an optical coherence tomography (OCT) imaging module.

FIG. 12 shows an example of an OCT image of an eye. The contacting surface of the applanation lens in the patient interface can be configured to have a curvature that minimizes distortions or folds in the cornea due to the pressure exerted on the eye during applanation. After the eye is successfully applanated at the patient interface, an OCT image can be obtained. As illustrated in FIG. 12, the curvature of the lens and cornea as well as the distances between the lens and cornea are identifiable in the OCT image. Subtler features such as the epithelium-cornea interface are detectable. Each of these identifiable features may be used as an internal reference of the laser coordinates with the eye. The coordinates of the cornea and lens can be digitized using well-established computer vision algorithms such as Edge or Blob detection. Once the coordinates of the lens are established, they can be used to control the focusing and positioning of the surgical laser beam for the surgery.

Alternatively, a calibration sample material may be used to form a 3-D array of reference marks at locations with known position coordinates. The OCT image of the calibration sample material can be obtained to establish a mapping relationship between the known position coordinates of the reference marks and the OCT images of the reference marks in the obtained OCT image. This mapping relationship is stored as digital calibration data and is applied in controlling the focusing and scanning of the surgical laser beam during the surgery in the target tissue based on the OCT images of the target tissue obtained during the surgery. The OCT imaging system is used here as an example and this calibration can be applied to images obtained via other imaging techniques.

In an imaging-guided laser surgical system described here, the surgical laser can produce relatively high peak powers sufficient to drive strong field/multi-photon ionization inside of the eye (i.e. inside of the cornea and lens) under high numerical aperture focusing. Under these conditions, one pulse from the surgical laser generates a plasma within the focal volume. Cooling of the plasma results in a well defined damage zone or "bubble" that may be used as a reference point. The following sections describe a calibration procedure for calibrating the surgical laser against an OCT-based imaging system using the damage zones created by the surgical laser.

Before surgery can be performed, the OCT is calibrated against the surgical laser to establish a relative positioning relationship so that the surgical laser can be controlled in position at the target tissue with respect to the position associated with images in the OCT image of the target tissue obtained by the OCT. One way for performing this calibration uses a pre-calibrated target or "phantom" which can be damaged by the laser as well as imaged with the OCT. The phantom can be fabricated from various materials such as a glass or hard plastic (e.g. PMMA) such that the material can permanently record optical damage created by the surgical laser. The phantom can also be selected to have optical or other properties (such as water content) that are similar to the surgical target.

The phantom can be, e.g., a cylindrical material having a diameter of at least 10 mm (or that of the scanning range of the delivery system) and a cylindrical length of at least 10 mm long spanning the distance of the epithelium to the crystalline lens of the eye, or as long as the scanning depth of the surgical system. The upper surface of the phantom can be curved to mate seamlessly with the patient interface or the phantom material may be compressible to allow full applanation. The phantom may have a three dimensional grid such that both the laser position (in x and y) and focus (z), as well as the OCT image can be referenced against the phantom.

Figure 13:
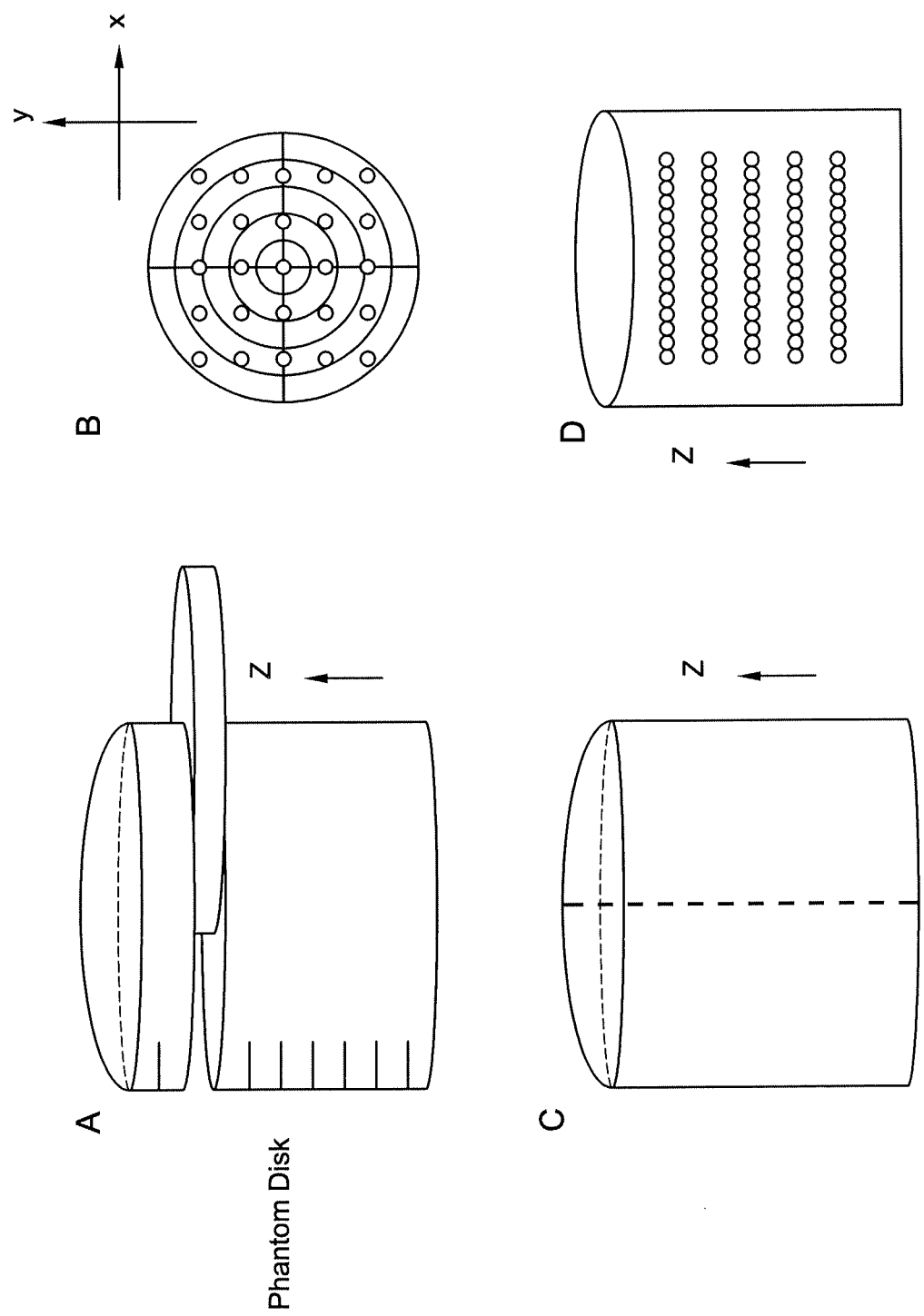
FIGS. 13A, 13B, 13C and 13D show two examples of calibration samples for calibrating an imaging-guided laser surgical system.

FIG. 13A-13D illustrate two exemplary configurations for the phantom. FIG. 13A illustrates a phantom that is segmented into thin disks. FIG. 13B shows a single disk patterned to have a grid of reference marks as a reference for determining the laser position across the phantom (i.e. the x- and y-coordinates). The z-coordinate (depth) can be determined by removing an individual disk from the stack and imaging it under a confocal microscope.

FIG. 13C illustrates a phantom that can be separated into two halves. Similar to the segmented phantom in FIG. 13A, this phantom is structured to contain a grid of reference marks as a reference for determining the laser position in the x- and y-coordinates. Depth information can be extracted by separating the phantom into the two halves and measuring the distance between damage zones. The combined information can provide the parameters for image guided surgery.

Figure 14:
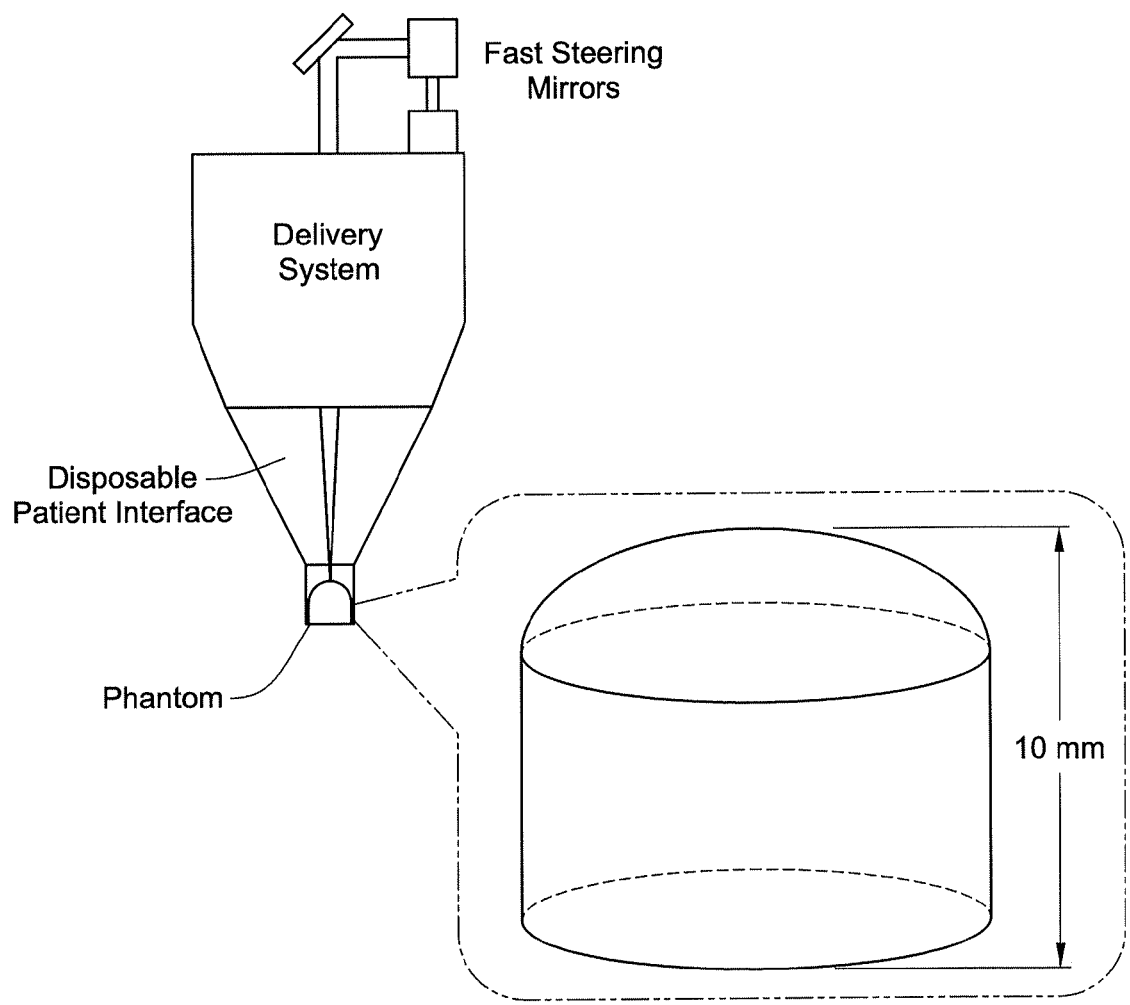
FIG. 14 shows an example of attaching a calibration sample material to a patient interface in an imaging-guided laser surgical system for calibrating the system.

FIG. 14 shows a surgical system part of the imaging-guided laser surgical system. This system includes steering mirrors which may be actuated by actuators such as galvanometers or voice coils, an objective lens e and a disposable patient interface. The surgical laser beam is reflected from the steering mirrors through the objective lens. The objective lens focuses the beam just after the patient interface. Scanning in the x- and y-coordinates is performed by changing the angle of the beam relative to the objective lens. Scanning in z-plane is accomplished by changing the divergence of the incoming beam using a system of lens upstream to the steering mirrors.

In this example, the conical section of the disposable patient interface may be either air spaced or solid and the section interfacing with the patient includes a curved contact lens. The curved contact lens can be fabricated from fused silica or other material resistant to forming color centers when irradiated with ionizing radiation. The radius of curvature is on the upper limit of what is compatible with the eye, e.g., about 10 mm.

The first step in the calibration procedure is docking the patient interface with the phantom. The curvature of the phantom matches the curvature of the patient interface. After docking, the next step in the procedure involves creating optical damage inside of the phantom to produce the reference marks.

Figure 15:
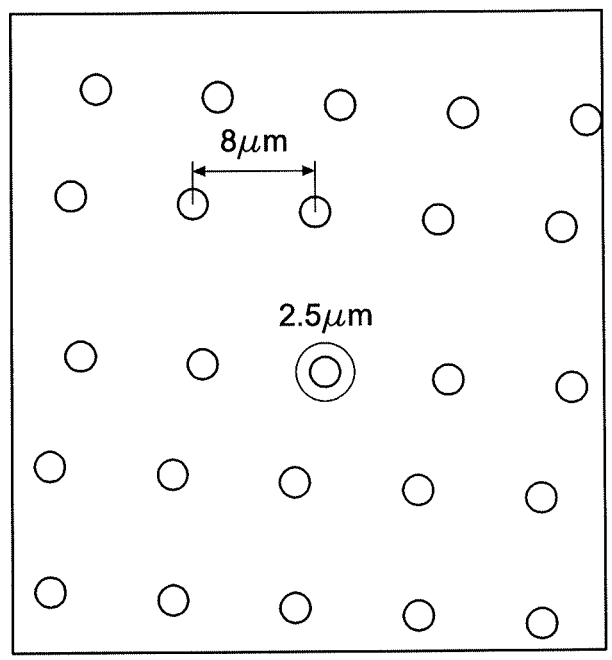
FIG. 15 shows an example of reference marks created by a surgical laser beam on a glass surface.

FIG. 15 shows examples of actual damage zones produced by a femtosecond laser in glass. The separation between the damage zones is on average 8 µm (the pulse energy is 2.2 µJ with duration of 580 fs at full width at half maximum). The optical damage depicted in FIG. 15 shows that the damage zones created by the femtosecond laser are well-defined and discrete. In the example shown, the damage zones have a diameter of about 2.5 µm. Optical damage zones similar to that shown in FIG. 14 are created in the phantom at various depths to form a 3-D array of the reference marks. These damage zones are referenced against the calibrated phantom either by extracting the appropriate disks and imaging it under a confocal microscope (FIG. 13A) or by splitting the phantom into two halves and measuring the depth using a micrometer (FIG. 13C). The x- and y-coordinates can be established from the pre-calibrated grid.

After damaging the phantom with the surgical laser, OCT on the phantom is performed. The OCT imaging system provides a 3D rendering of the phantom establishing a relationship between the OCT coordinate system and the phantom. The damage zones are detectable with the imaging system. The OCT and laser may be cross-calibrated using the phantom's internal standard. After the OCT and the laser are referenced against each other, the phantom can be discarded.

Prior to surgery, the calibration can be verified. This verification step involves creating optical damage at various positions inside of a second phantom. The optical damage should be intense enough such that the multiple damage zones which create a circular pattern can be imaged by the OCT. After the pattern is created, the second phantom is imaged with the OCT. Comparison of the OCT image with the laser coordinates provides the final check of the system calibration prior to surgery.

Once the coordinates are fed into the laser, laser surgery can be performed inside the eye. This involves photo-emulsification of the lens using the laser, as well as other laser treatments to the eye. The surgery can be stopped at any time and the anterior segment of the eye (FIG. 11) can be re-imaged to monitor the progress of the surgery; moreover, after an intraocular lens (IOL) is inserted, imaging the IOL (with light or no applanation) provides information regarding the position of the IOL in the eye. This information may be utilized by the physician to refine the position of IOL.

Figure 16A:
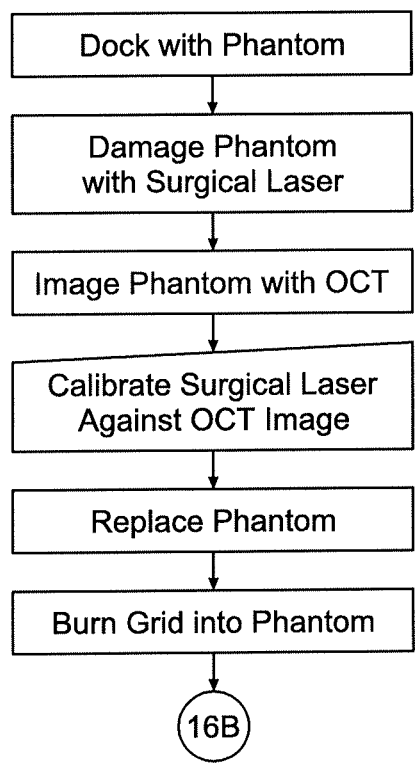
FIGS. 16A and 16B show an example of the calibration process and the post-calibration surgical operation for an imaging-guided laser surgical system.
Figure 16B:
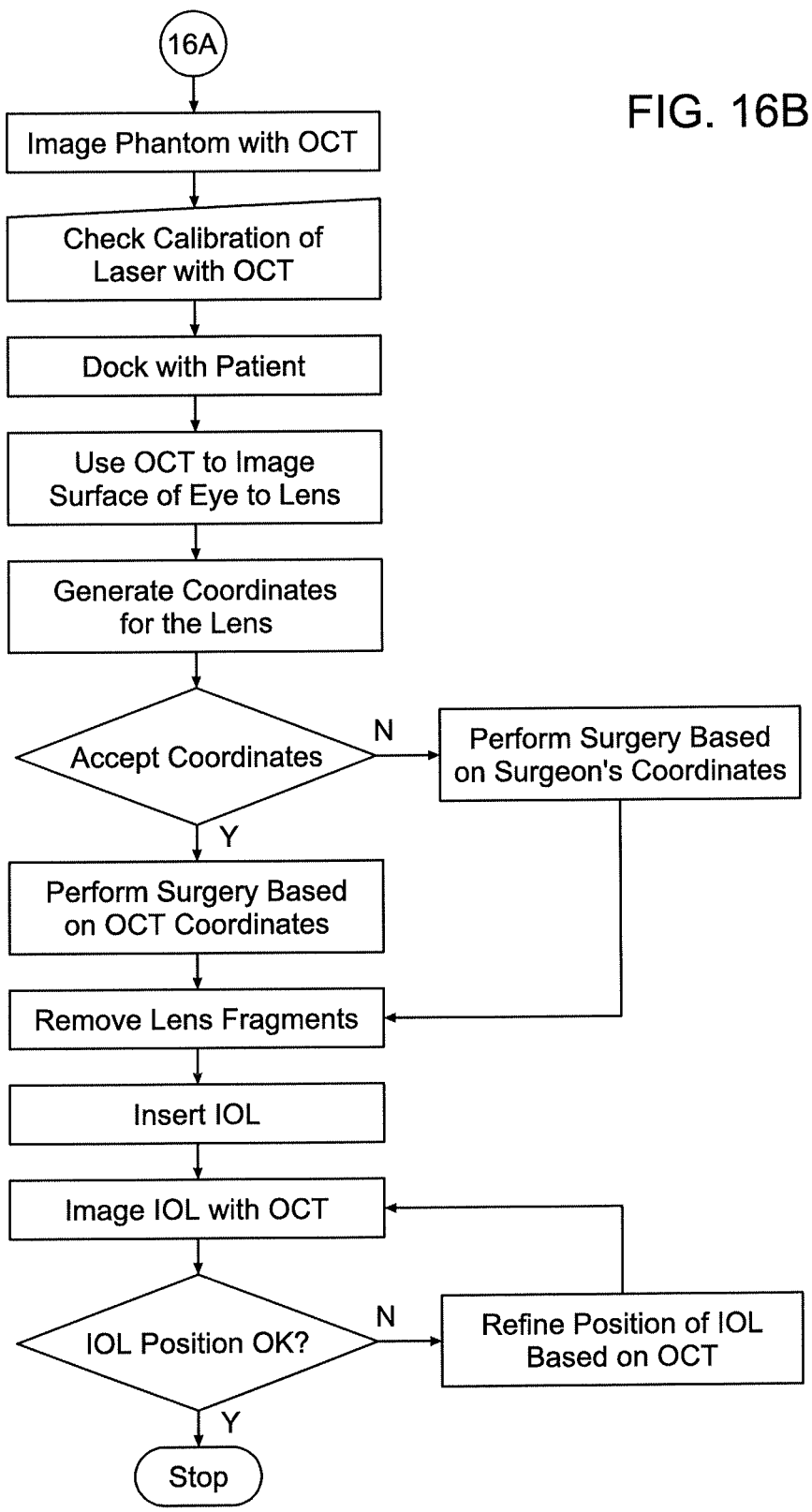

FIG. 16 shows an example of the calibration process and the post-calibration surgical operation. This examples illustrates a method for performing laser surgery by using an imaging-guided laser surgical system can include using a patient interface in the system, that is engaged to hold a target tissue under surgery in position, to hold a calibration sample material during a calibration process before performing a surgery; directing a surgical laser beam of laser pulses from a laser in the system to the patient interface into the calibration sample material to burn reference marks at selected three-dimensional reference locations; directing an optical probe beam from an optical coherence tomography (OCT) module in the system to the patient interface into the calibration sample material to capture OCT images of the burnt reference marks; and establishing a relationship between positioning coordinates of the OCT module and the burnt reference marks. After the establishing the relationship, a patient interface in the system is used to engage to and to hold a target tissue under surgery in position. The surgical laser beam of laser pulses and the optical probe beam are directed to the patient interface into the target tissue. The surgical laser beam is controlled to perform laser surgery in the target tissue. The OCT module is operated to obtain OCT images inside the target tissue from light of the optical probe beam returning from the target tissue and the position information in the obtained OCT images and the established relationship are applied in focusing and scanning of the surgical laser beam to adjust the focusing and scanning of the surgical laser beam in the target tissue during surgery. While such calibrations can be performed immediately prior to laser surgery, they can also be performed at various intervals before a procedure, using calibration validations that demonstrated a lack of drift or change in calibration during such intervals.

The following examples describe imaging-guided laser surgical techniques and systems that use images of laser-induced photodisruption byproducts for alignment of the surgical laser beam.

FIGS. 17A and 17B illustrates another implementation of the present technique in which actual photodisruption byproducts in the target tissue are used to guide further laser placement. A pulsed laser 1710, such as a femtosecond or picosecond laser, is used to produce a laser beam 1712 with laser pulses to cause photodisruption in a target tissue 1001. The target tissue 1001 may be a part of a body part 1700 of a subject, e.g., a portion of the lens of one eye. The laser beam 1712 is focused and directed by an optics module for the laser 1710 to a target tissue position in the target tissue 1001 to achieve a certain surgical effect. The target surface is optically coupled to the laser optics module by an applanation plate 1730 that transmits the laser wavelength, as well as image wavelengths from the target tissue. The applanation plate 1730 can be an applanation lens. An imaging device 1720 is provided to collect reflected or scattered light or sound from the target tissue 1001 to capture images of the target tissue 1001 either before or after (or both) the applanation plate is applied. The captured imaging data is then processed by the laser system control module to determine the desired target tissue position. The laser system control module moves or adjusts optical or laser elements based on standard optical models to ensure that the center of photodisruption byproduct 1702 overlaps with the target tissue position. This can be a dynamic alignment process where the images of the photodisruption byproduct 1702 and the target tissue 1001 are continuously monitored during the surgical process to ensure that the laser beam is properly positioned at each target tissue position.

In one implementation, the laser system can be operated in two modes: first in a diagnostic mode in which the laser beam 1712 is initially aligned by using alignment laser pulses to create photodisruption byproduct 1702 for alignment and then in a surgical mode where surgical laser pulses are generated to perform the actual surgical operation. In both modes, the images of the disruption byproduct 1702 and the target tissue 1001 are monitored to control the beam alignment. FIG. 17A shows the diagnostic mode where the alignment laser pulses in the laser beam 1712 may be set at a different energy level than the energy level of the surgical laser pulses. For example, the alignment laser pulses may be less energetic than the surgical laser pulses but sufficient to cause significant photodisruption in the tissue to capture the photodisruption byproduct 1702 at the imaging device 1720. The resolution of this coarse targeting may not be sufficient to provide desired surgical effect. Based on the captured images, the laser beam 1712 can be aligned properly. After this initial alignment, the laser 1710 can be controlled to produce the surgical laser pulses at a higher energy level to perform the surgery. Because the surgical laser pulses are at a different energy level than the alignment laser pulses, the nonlinear effects in the tissue material in the photodisruption can cause the laser beam 1712 to be focused at a different position from the beam position during the diagnostic mode. Therefore, the alignment achieved during the diagnostic mode is a coarse alignment and additional alignment can be further performed to precisely position each surgical laser pulse during the surgical mode when the surgical laser pulses perform the actual surgery. Referring to FIG. 17A, the imaging device 1720 captures the images from the target tissue 1001 during the surgical mode and the laser control module adjust the laser beam 1712 to place the focus position 1714 of the laser beam 1712 onto the desired target tissue position in the target tissue 1001. This process is performed for each target tissue position.

Figure 18:
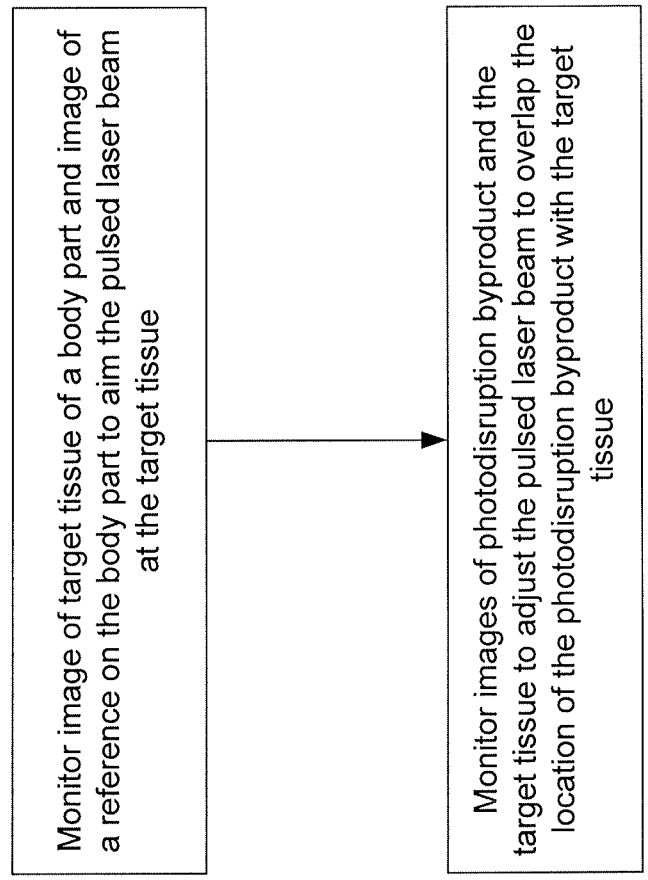
FIGS. 18 and 19 show examples of laser alignment operations in imaging-guided laser surgical systems.

FIG. 18 shows one implementation of the laser alignment where the laser beam is first approximately aimed at the target tissue and then the image of the photodisruption byproduct is captured and used to align the laser beam. The image of the target tissue of the body part as the target tissue and the image of a reference on the body part are monitored to aim the pulsed laser beam at the target tissue. The images of photodisruption byproduct and the target tissue are used to adjust the pulsed laser beam to overlap the location of the photodisruption byproduct with the target tissue.

Figure 19:
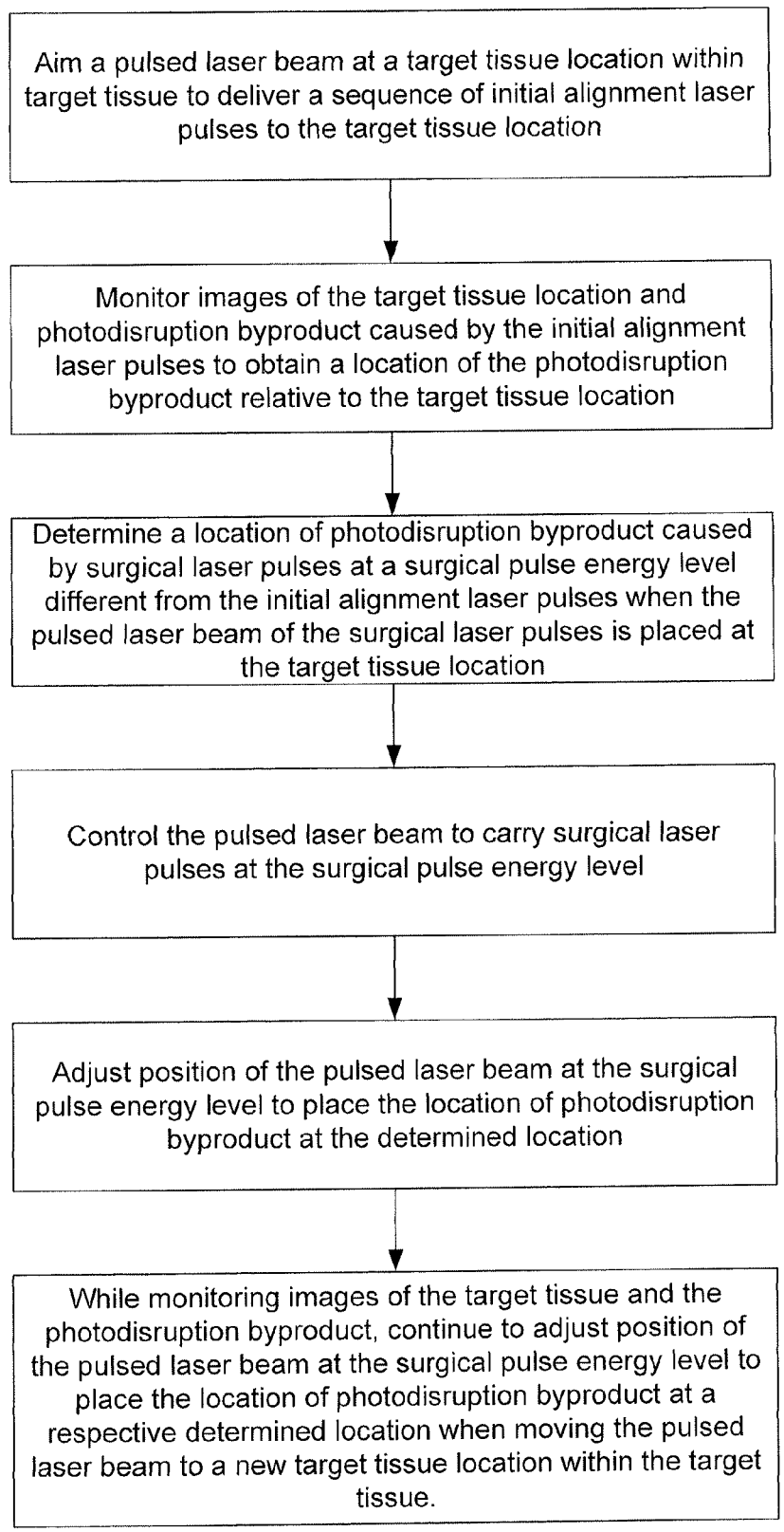

FIG. 19 shows one implementation of the laser alignment method based on imaging photodisruption byproduct in the target tissue in laser surgery. In this method, a pulsed laser beam is aimed at a target tissue location within target tissue to deliver a sequence of initial alignment laser pulses to the target tissue location. The images of the target tissue location and photodisruption byproduct caused by the initial alignment laser pulses are monitored to obtain a location of the photodisruption byproduct relative to the target tissue location. The location of photodisruption byproduct caused by surgical laser pulses at a surgical pulse energy level different from the initial alignment laser pulses is determined when the pulsed laser beam of the surgical laser pulses is placed at the target tissue location. The pulsed laser beam is controlled to carry surgical laser pulses at the surgical pulse energy level. The position of the pulsed laser beam is adjusted at the surgical pulse energy level to place the location of photodisruption byproduct at the determined location. While monitoring images of the target tissue and the photodisruption byproduct, the position of the pulsed laser beam at the surgical pulse energy level is adjusted to place the location of photodisruption byproduct at a respective determined location when moving the pulsed laser beam to a new target tissue location within the target tissue.

Figure 20:
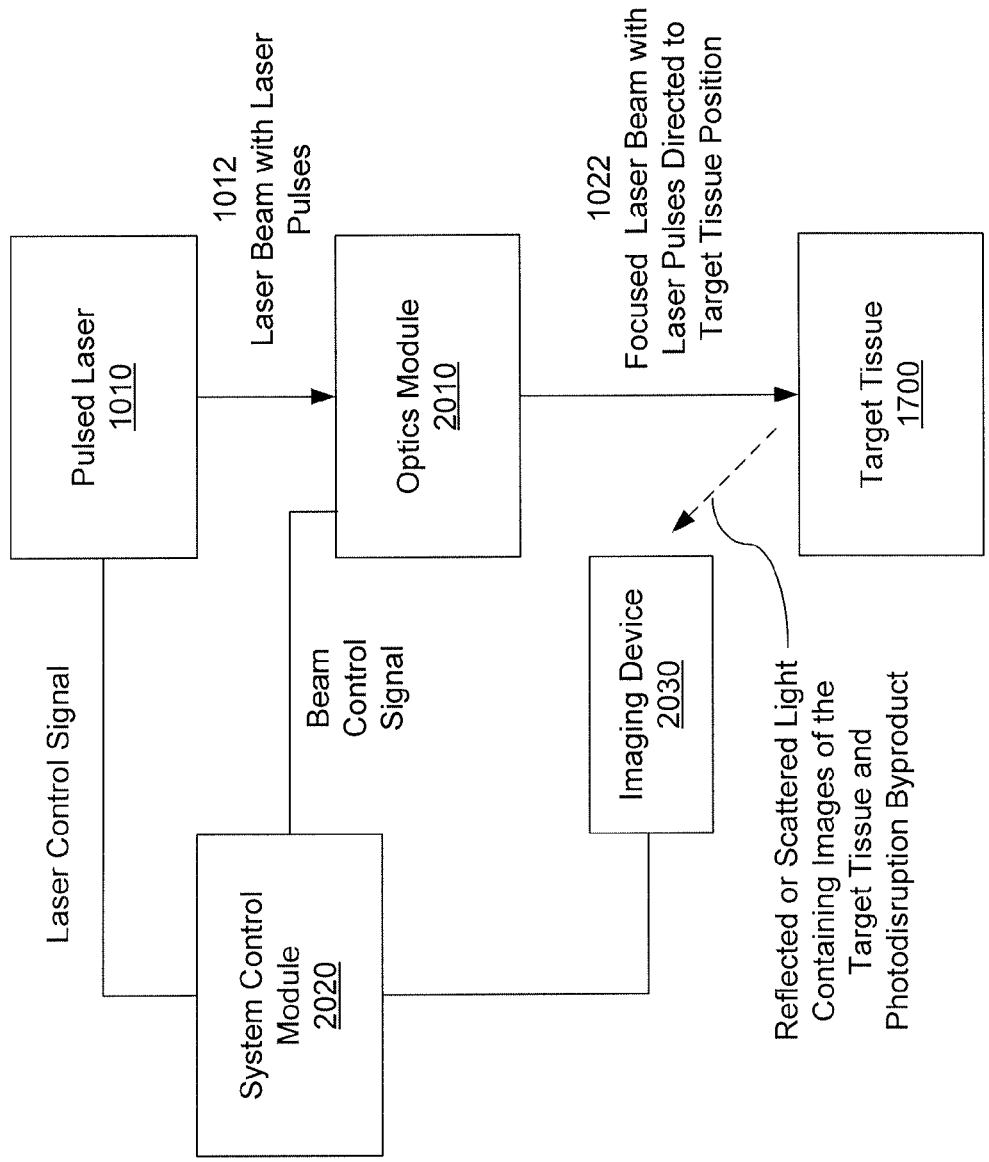
FIG. 20 shows an exemplary laser surgical system based on the laser alignment using the image of the photodisruption byproduct.

FIG. 20 shows an exemplary laser surgical system based on the laser alignment using the image of the photodisruption byproduct. An optics module 2010 is provided to focus and direct the laser beam to the target tissue 1700. The optics module 2010 can include one or more lenses and may further include one or more reflectors. A control actuator is included in the optics module 2010 to adjust the focusing and the beam direction in response to a beam control signal. A system control module 2020 is provided to control both the pulsed laser 1010 via a laser control signal and the optics module 2010 via the beam control signal. The system control module 2020 processes image data from the imaging device 2030 that includes the position offset information for the photodisruption byproduct 1702 from the target tissue position in the target tissue 1700. Based on the information obtained from the image, the beam control signal is generated to control the optics module 2010 which adjusts the laser beam. A digital processing unit is included in the system control module 2020 to perform various data processing for the laser alignment.

The imaging device 2030 can be implemented in various forms, including an optical coherent tomography (OCT) device. In addition, an ultrasound imaging device can also be used. The position of the laser focus is moved so as to place it grossly located at the target at the resolution of the imaging device. The error in the referencing of the laser focus to the target and possible non-linear optical effects such as self focusing that make it difficult to accurately predict the location of the laser focus and subsequent photodisruption event. Various calibration methods, including the use of a model system or software program to predict focusing of the laser inside a material can be used to get a coarse targeting of the laser within the imaged tissue. The imaging of the target can be performed both before and after the photodisruption. The position of the photodisruption by products relative to the target is used to shift the focal point of the laser to better localize the laser focus and photodisruption process at or relative to the target. Thus the actual photodisruption event is used to provide a precise targeting for the placement of subsequent surgical pulses.

Photodisruption for targeting during the diagnostic mode can be performed at a lower, higher or the same energy level that is required for the later surgical processing in the surgical mode of the system. A calibration may be used to correlate the localization of the photodisruptive event performed at a different energy in diagnostic mode with the predicted localization at the surgical energy because the optical pulse energy level can affect the exact location of the photodisruptive event. Once this initial localization and alignment is performed, a volume or pattern of laser pulses (or a single pulse) can be delivered relative to this positioning. Additional sampling images can be made during the course of delivering the additional laser pulses to ensure proper localization of the laser (the sampling images may be obtained with use of lower, higher or the same energy pulses). In one implementation, an ultrasound device is used to detect the cavitation bubble or shock wave or other photodisruption byproduct. The localization of this can then be correlated with imaging of the target, obtained via ultrasound or other modality. In another embodiment, the imaging device is simply a biomicroscope or other optical visualization of the photodisruption event by the operator, such as optical coherence tomography. With the initial observation, the laser focus is moved to the desired target position, after which a pattern or volume of pulses is delivered relative to this initial position.

As a specific example, a laser system for precise subsurface photodisruption can include means for generating laser pulses capable of generating photodisruption at repetition rates of 100-1000 Million pulses per second, means for coarsely focusing laser pulses to a target below a surface using an image of the target and a calibration of the laser focus to that image without creating a surgical effect, means for detecting or visualizing below a surface to provide an image or visualization of a target the adjacent space or material around the target and the byproducts of at least one photodisruptive event coarsely localized near the target, means for correlating the position of the byproducts of photodisruption with that of the sub surface target at least once and moving the focus of the laser pulse to position the byproducts of photodisruption at the sub surface target or at a relative position relative to the target, means for delivering a subsequent train of at least one additional laser pulse in pattern relative to the position indicated by the above fine correlation of the byproducts of photodisruption with that of the sub surface target, and means for continuing to monitor the photodisruptive events during placement of the subsequent train of pulses to further fine tune the position of the subsequent laser pulses relative to the same or revised target being imaged.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

A number of implementations of imaging-guided laser surgical techniques, apparatus and systems are disclosed. However, variations and enhancements of the described implementations, and other implementations can be made based on what is described.

What is claimed is:

1. A laser surgical system, comprising:
a pulsed laser source, configured to produce a laser beam of laser pulses;
an optics module configured
to receive the laser beam from the pulsed laser source,
to direct the laser beam into a lens of an eye, and
to scan the laser beam in the lens of the eye;
an Optical Coherence Tomography (OCT) imaging device, configured to create an OCT image of the lens of the eye;
a non-OCT imaging device, configured to generate a non-OCT image of the eye; and
a system control module, configured
to register the eye to the laser surgical system based on the non-OCT image, and
to control the optics module directing and scanning the laser beam based on the registering wherein the non-OCT imaging device is configured to generate the non-OCT image before an applanation plate is applied to couple the laser surgical system to the eye, and the system control module is configured to control the placement of the laser pulses using the registering of the eye based on the non-OCT image, and the OCT image.

2. The laser surgical system of claim 1, wherein:
the non-OCT imaging device is one of a microscope, a video microscope, a video camera, a CCD-sensor array, and a CMS-sensor array.

3. The laser surgical system of claim 1, wherein:
the laser surgical system includes a diagnostic instrument; and
the system control module is configured to augment the non-OCT image with pre-operative information generated by the diagnostic instrument.

4. The laser surgical system of claim 3, wherein:
the diagnostic instrument comprises at least one of a wavefront aberrometer and a corneal topography measuring device.

5. The laser surgical system of claim 1, wherein:
the non-OCT imaging device is configured to generate
a pre-applanation non-OCT image before an applanation plate is applied to couple the laser surgical system to the eye, and
a post-applanation non-OCT image after the applanation plate is applied to couple the laser surgical system to the eye.

6. The laser surgical system of claim 5, wherein:
the system control module is configured to register the eye to the laser surgical system based on the pre-applanation non-OCT image and the post-applanation non-OCT image.

7. The laser surgical system of claim 1, wherein:
the system control module is configured to control the placement of the laser pulses for at least one of a cutting and a volume disruption.

8. The laser surgical system of claim 1, wherein:
the system control module is configured to register the eye without a complete non-OCT image.

9. The laser surgical system of claim 1, wherein:
the non-OCT imaging device comprises a third optical channel, at least partially separate from the optics module and from the OCT imaging device.

10. A method of performing laser surgery, the method comprising:
generating a non-Optical Coherence Tomography (non-OCT) image of an eye with a non-OCT imaging device comprising generating a non-OCT image before an applanation plate is applied to couple the laser surgical system to the eye;
registering the eye to a laser surgical system by a system control module based on the non-OCT image;
generating an OCT image of the eye;
generating laser pulses by a pulsed laser source;
directing and scanning the laser pulses in the eye by an optics module; and
controlling a placement of the laser pulses by the system control module based on the registering of the eye by the non-OCT image, and the OCT image.

11. The method of claim 10, wherein the laser surgical system includes a diagnostic instrument, the method comprising:
generating pre-operative information by the diagnostic instrument; and
augmenting the non-OCT image by the system control module based on the pre-operative information generated by the diagnostic instrument.

12. The method of claim 10, the generating a non-OCT image further comprises
generating a post-applanation non-OCT image after the applanation plate is applied to couple the laser surgical system to the eye.

13. The method of claim 12, the registering comprising:
registering the eye to the laser surgical system by the system control module based on the pre-applanation non-OCT image and the post-applanation non-OCT image.

* * * * *